United States Patent
Abdou

(10) Patent No.: US 9,107,705 B2
(45) Date of Patent: Aug. 18, 2015

(54) DYNAMIC SPINAL STABILIZATION SYSTEMS AND METHODS OF USE

(76) Inventor: M. Samy Abdou, San Diego, CA (US)

(*) Notice: Subject to any disclaimer, the term of this patent is extended or adjusted under 35 U.S.C. 154(b) by 1636 days.

(21) Appl. No.: 11/954,069

(22) Filed: Dec. 11, 2007

(65) Prior Publication Data

US 2008/0281358 A1 Nov. 13, 2008

(51) Int. Cl.
  *A61B 17/70* (2006.01)
  *A61F 2/44* (2006.01)
  *A61F 2/30* (2006.01)

(52) U.S. Cl.
  CPC ......... *A61B 17/7067* (2013.01); *A61B 17/7023* (2013.01); *A61B 17/7025* (2013.01); *A61B 17/7043* (2013.01); *A61B 17/7062* (2013.01); *A61F 2/442* (2013.01); *A61F 2/4425* (2013.01); *A61B 17/7005* (2013.01); *A61B 17/7032* (2013.01); *A61F 2002/30224* (2013.01); *A61F 2002/30471* (2013.01); *A61F 2002/30565* (2013.01); *A61F 2002/30571* (2013.01); *A61F 2002/30578* (2013.01); *A61F 2002/443* (2013.01); *A61F 2220/0091* (2013.01); *A61F 2230/0069* (2013.01)

(58) Field of Classification Search
  CPC .................. A61B 17/7043; A61B 17/7067
  USPC ................ 606/246–249; 623/17.11–17.16
  See application file for complete search history.

(56) References Cited

U.S. PATENT DOCUMENTS

| | | | |
|---|---|---|---|
| 4,759,769 A | 7/1988 | Hedman et al. | |
| 5,425,773 A | 6/1995 | Boyd et al. | |
| 5,556,431 A | 9/1996 | Buttner-Janz | |
| 5,562,738 A | 10/1996 | Boyd et al. | |
| 5,674,296 A | 10/1997 | Bryan et al. | |
| 5,676,701 A | 10/1997 | Yuan et al. | |
| 6,179,873 B1 | 1/2001 | Zientek | |
| 6,355,038 B1 | 3/2002 | Pisharodi | |
| 6,527,803 B1 | 3/2003 | Crozet et al. | |
| 6,610,093 B1 * | 8/2003 | Pisharodi | 623/17.15 |
| 6,770,096 B2 | 8/2004 | Bolger et al. | |
| 7,083,622 B2 | 8/2006 | Simonson | |
| 7,282,065 B2 * | 10/2007 | Kirschman | 623/17.15 |
| 7,594,932 B2 | 9/2009 | Aferzon et al. | |

(Continued)

FOREIGN PATENT DOCUMENTS

| | | |
|---|---|---|
| WO | WO 2007/095333 | 8/2007 |
| WO | WO 2007/140382 | 12/2007 |

(Continued)

OTHER PUBLICATIONS

Abdou, Inter-Vertebral Disc Prosthesis With Variable Rotational Stop and Methods of Use, Apr. 23, 2007, U.S. Appl. No. 11/739,053.

(Continued)

*Primary Examiner* — Matthew Lawson

(74) *Attorney, Agent, or Firm* — Gazdzinski & Associates PC

(57) ABSTRACT

In a spinal implant device, a frictionless pivot member is used to interconnect multiple links and produce a scissor jack-like device with minimal frictional wear characteristics. The device is attached to at least two vertebrae, wherein a first device segment is attached to a first vertebra and at least one additional device segment is attached to at least one additional vertebra. The implanted device functions to control and dampen the movement between the attached vertebral bodies.

22 Claims, 46 Drawing Sheets

(56) References Cited

U.S. PATENT DOCUMENTS

| | | | |
|---|---|---|---|
| 7,695,517 B2 | 4/2010 | Benzel et al. | |
| 7,727,280 B2 | 6/2010 | McLuen | |
| 7,749,274 B2 | 7/2010 | Razian | |
| 7,799,081 B2 | 9/2010 | McKinley | |
| 7,879,074 B2 * | 2/2011 | Kwak et al. | 606/257 |
| 7,922,745 B2 * | 4/2011 | Hestad et al. | 606/249 |
| 8,172,855 B2 | 5/2012 | Abdou | |
| 2001/0039452 A1 | 11/2001 | Zucherman et al. | |
| 2003/0065395 A1 | 4/2003 | Ralph et al. | |
| 2003/0078662 A1 | 4/2003 | Ralph et al. | |
| 2003/0217809 A1 | 11/2003 | Morishige | |
| 2004/0049280 A1 | 3/2004 | Cauthen | |
| 2004/0143264 A1 | 7/2004 | McAfee | |
| 2004/0225364 A1 | 11/2004 | Richelsoph et al. | |
| 2004/0236425 A1 | 11/2004 | Huang | |
| 2005/0033431 A1 | 2/2005 | Gordon et al. | |
| 2005/0043800 A1 | 2/2005 | Paul et al. | |
| 2005/0071007 A1 | 3/2005 | Malek | |
| 2005/0216083 A1 | 9/2005 | Michelson | |
| 2006/0069436 A1 | 3/2006 | Sutton et al. | |
| 2006/0069438 A1 | 3/2006 | Zucherman | |
| 2006/0084988 A1 | 4/2006 | Kim | |
| 2006/0217710 A1 | 9/2006 | Abdou | |
| 2007/0043356 A1 * | 2/2007 | Timm et al. | 606/61 |
| 2007/0093828 A1 | 4/2007 | Abdou | |
| 2007/0123884 A1 | 5/2007 | Abdou | |
| 2007/0161992 A1 | 7/2007 | Kwak et al. | |
| 2007/0185367 A1 | 8/2007 | Abdou | |
| 2007/0185489 A1 | 8/2007 | Abdou | |
| 2007/0191958 A1 | 8/2007 | Abdou et al. | |
| 2007/0198090 A1 | 8/2007 | Abdou | |
| 2007/0233251 A1 | 10/2007 | Abdou | |
| 2007/0270838 A1 * | 11/2007 | Bruneau et al. | 606/61 |
| 2007/0282448 A1 | 12/2007 | Abdou | |
| 2008/0027438 A1 | 1/2008 | Abdou | |
| 2008/0027550 A1 | 1/2008 | Link et al. | |
| 2008/0039843 A1 | 2/2008 | Abdou | |
| 2008/0045963 A1 | 2/2008 | Abdou | |
| 2008/0281359 A1 | 11/2008 | Abdou | |
| 2010/0016906 A1 | 1/2010 | Abdou | |
| 2010/0069929 A1 | 3/2010 | Abdou | |
| 2010/0069965 A1 | 3/2010 | Abdou | |
| 2010/0087858 A1 | 4/2010 | Abdou | |
| 2010/0087869 A1 | 4/2010 | Abdou | |
| 2010/0087878 A1 | 4/2010 | Abdou | |
| 2010/0087923 A1 | 4/2010 | Abdou | |
| 2010/0106250 A1 | 4/2010 | Abdou | |
| 2010/0121384 A1 | 5/2010 | Abdou | |
| 2010/0211177 A1 | 8/2010 | Abdou | |
| 2010/0268281 A1 | 10/2010 | Abdou | |
| 2010/0312282 A1 | 12/2010 | Abdou | |
| 2010/0318128 A1 | 12/2010 | Abdou | |
| 2010/0331889 A1 | 12/2010 | Abdou | |
| 2011/0004248 A1 | 1/2011 | Abdou | |
| 2011/0082553 A1 | 4/2011 | Abdou | |
| 2011/0172772 A1 | 7/2011 | Abdou | |

FOREIGN PATENT DOCUMENTS

| | | |
|---|---|---|
| WO | WO 2008/021319 | 2/2008 |
| WO | WO 2008/073447 | 6/2008 |

OTHER PUBLICATIONS

Abdou, Devices and Methods for Superior Fixation of Orthopedic Devices Onto the Vertebral Column, Aug. 1, 2007, U.S. Appl. No. 11/888,754.

Abdou, Spinous Process Fusion and Orthopedic Implants and Methods, Mar. 19, 2007, U.S. Appl. No. 12/727,641.

Abdou, Dynamic Bone Screw Assembly for Spinal Stabilization and Methods of Use, Apr. 12, 2010, U.S. Appl. No. 12/758,531.

Abdou, Inter-Vertebral Disc Prosthesis With Variable Rotational Stop and Methods of Use, May 27, 2010, U.S. Appl. No. 12/789,435.

Abdou, Spinal Fixation Devices and Methods of Use, Nov. 5, 2010, U.S. Appl. No. 12/940,960.

Abdou, Devices and Methods for Minimally Invasive Spinal Stabilization and Instrumentation, Dec. 7, 2010, U.S. Appl. No. 12/962,534.

Abdou, Variable-Shaped, Expandable Device and Method for Minimally-Invasive Use, Mar. 28, 2011, U.S. Appl. No. 13/073,860.

* cited by examiner

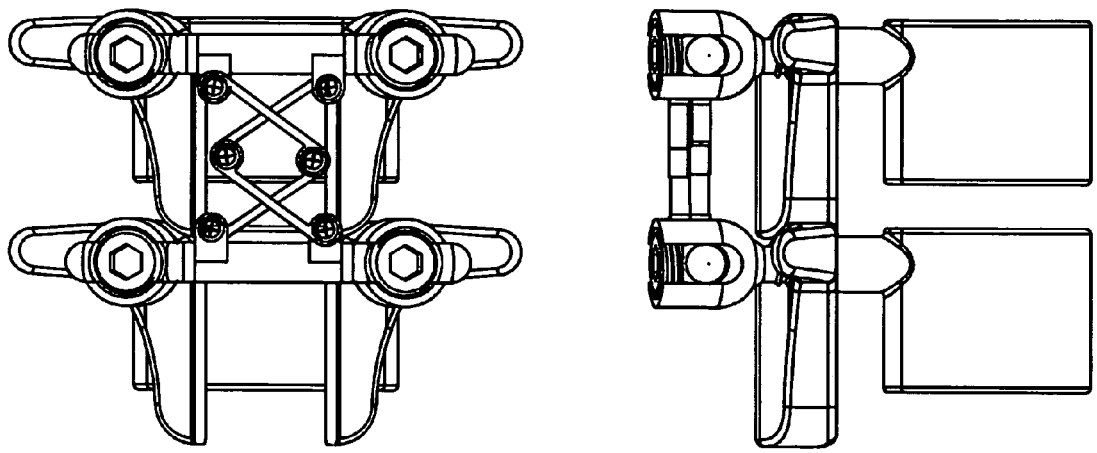
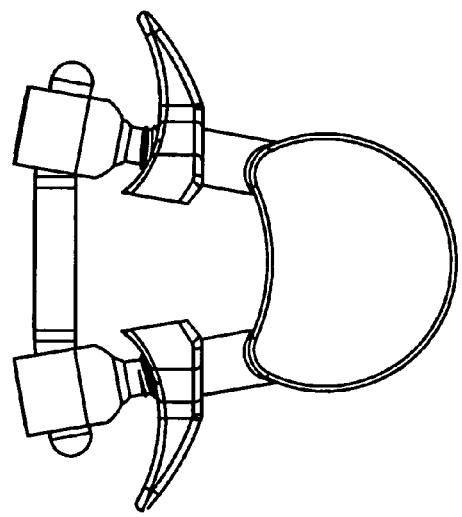
Fig. 2

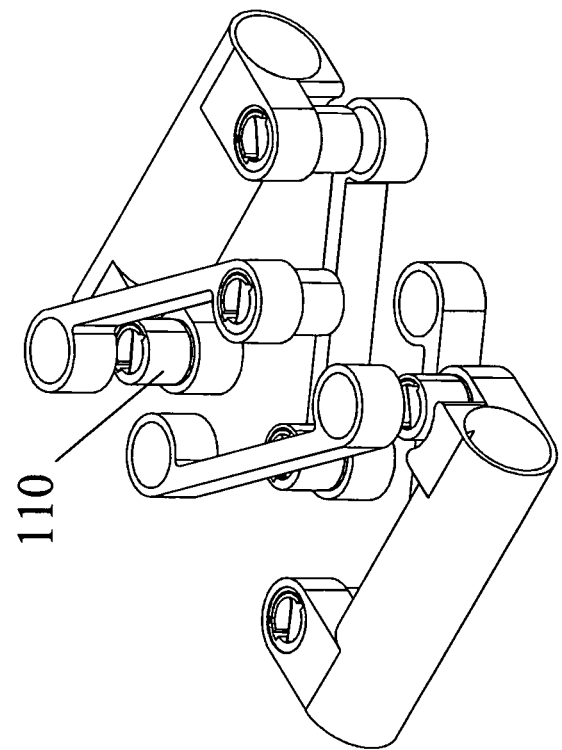
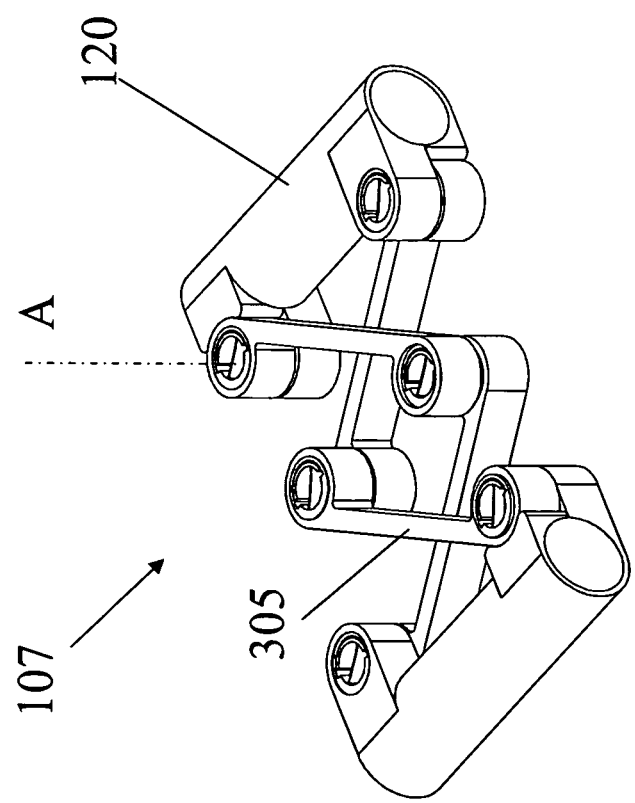
Fig. 3A
Fig. 3B

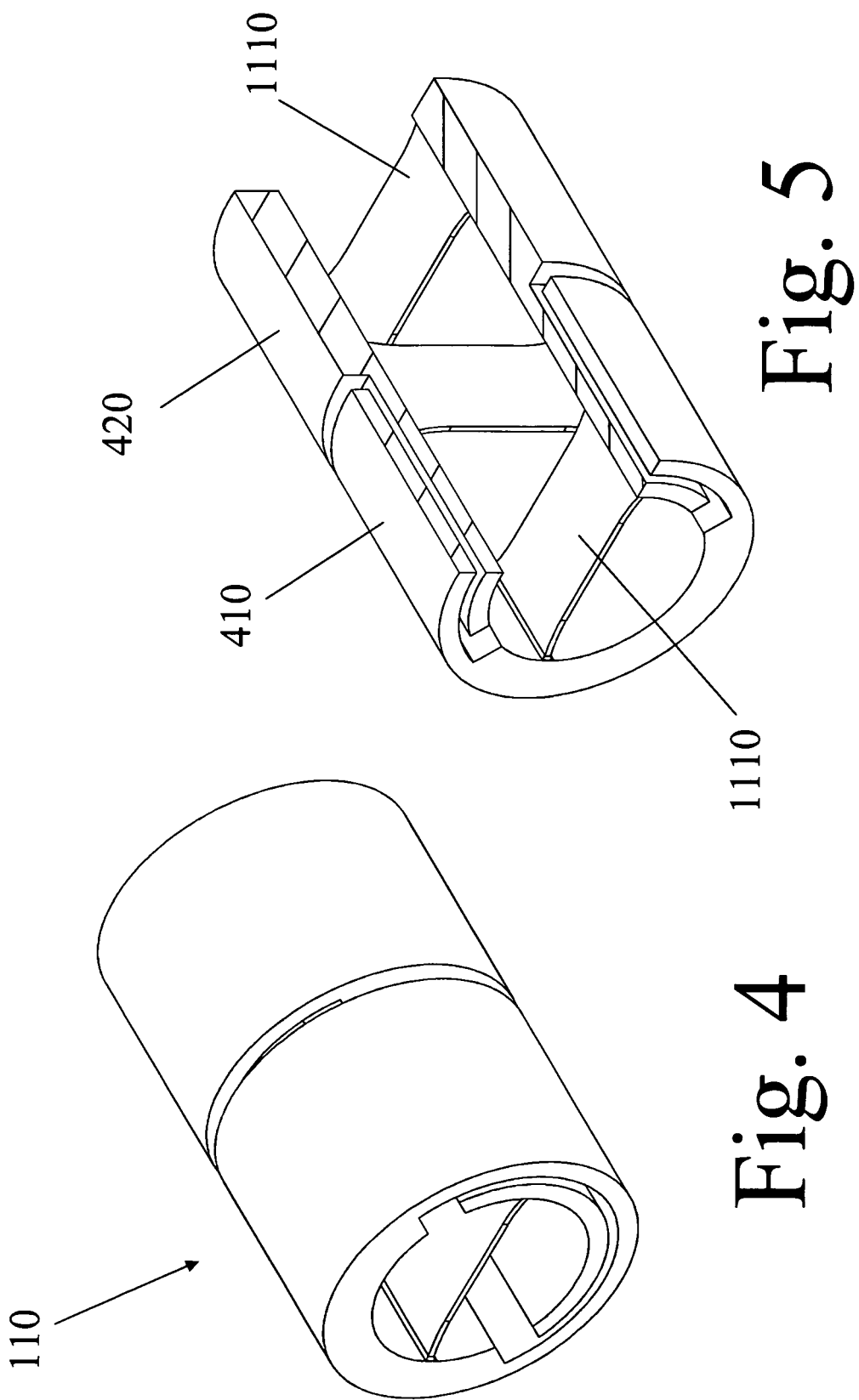

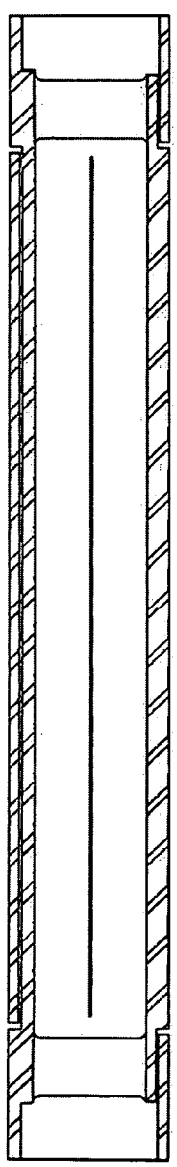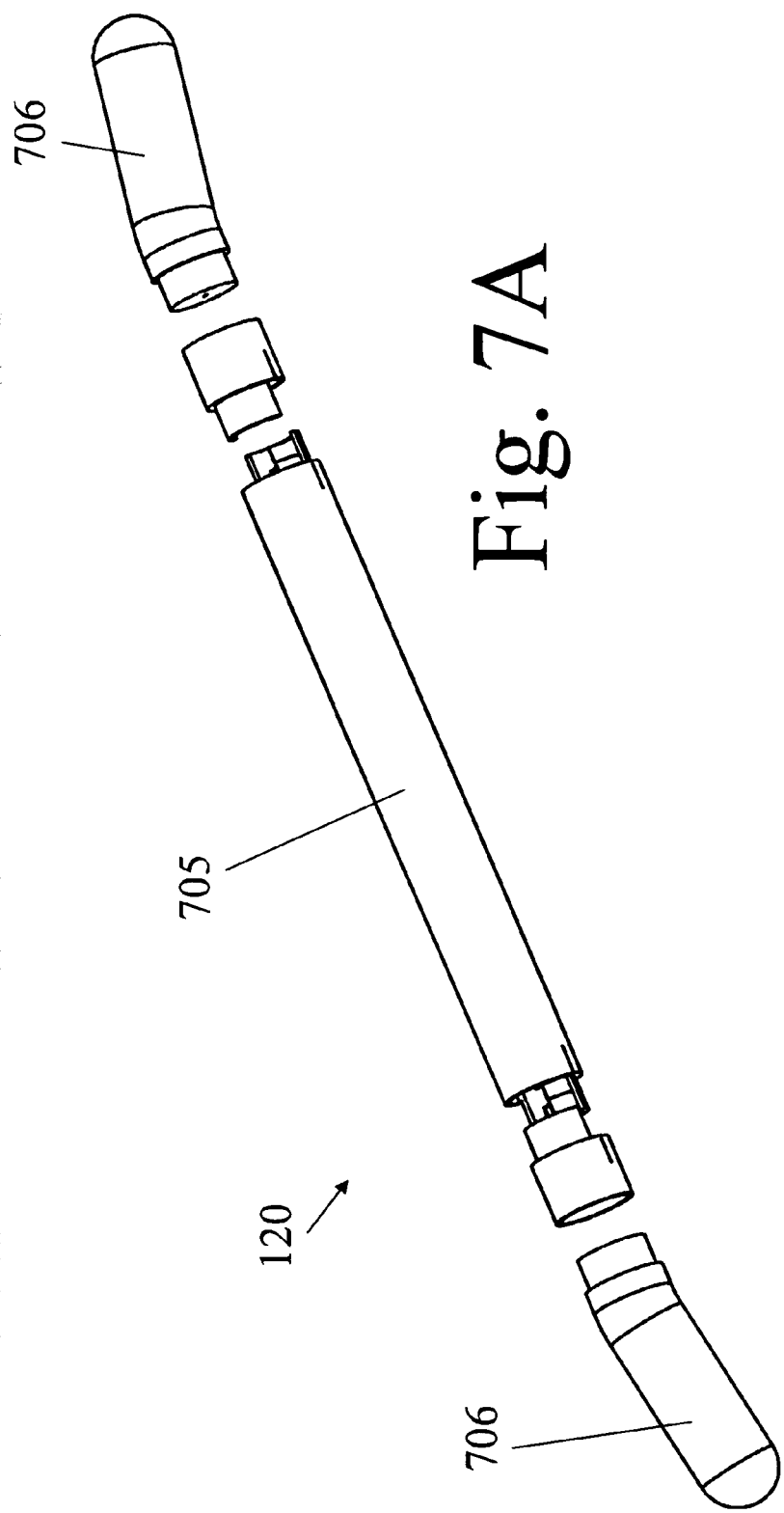

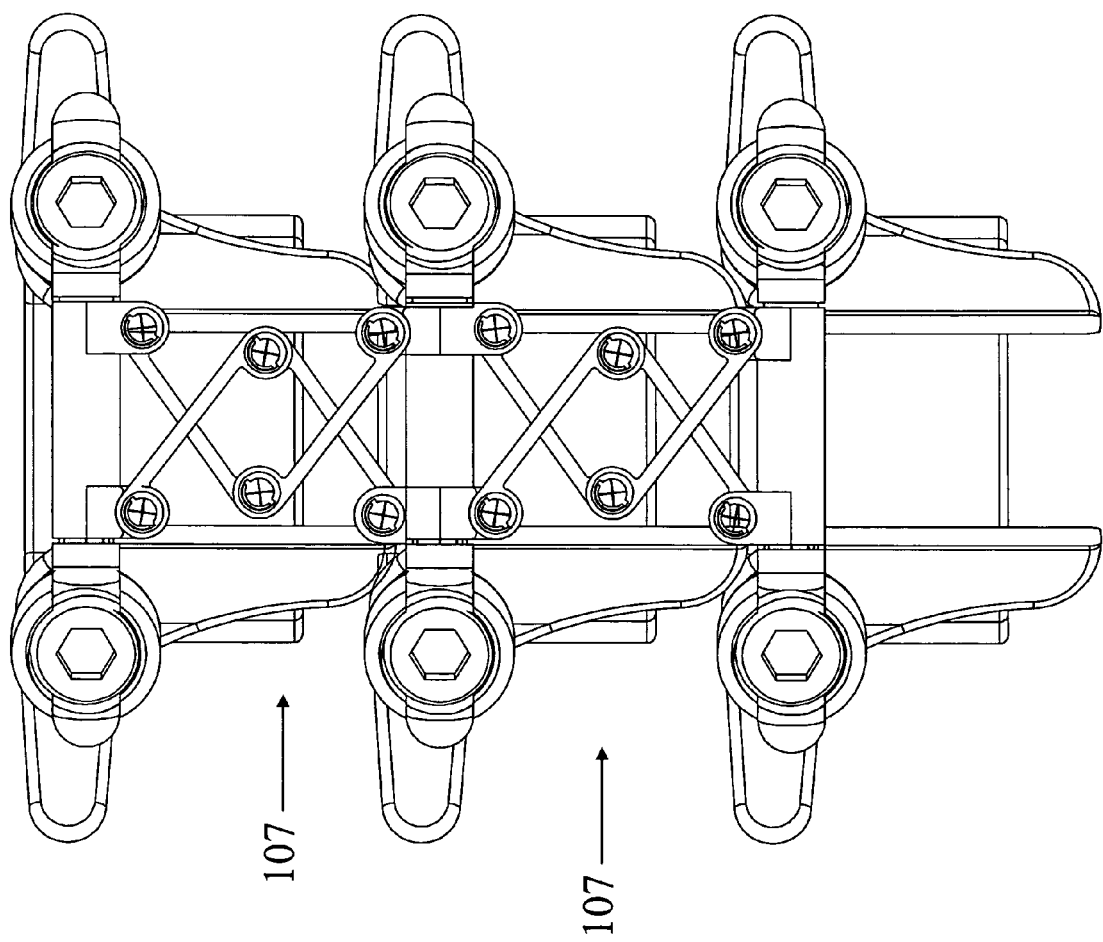

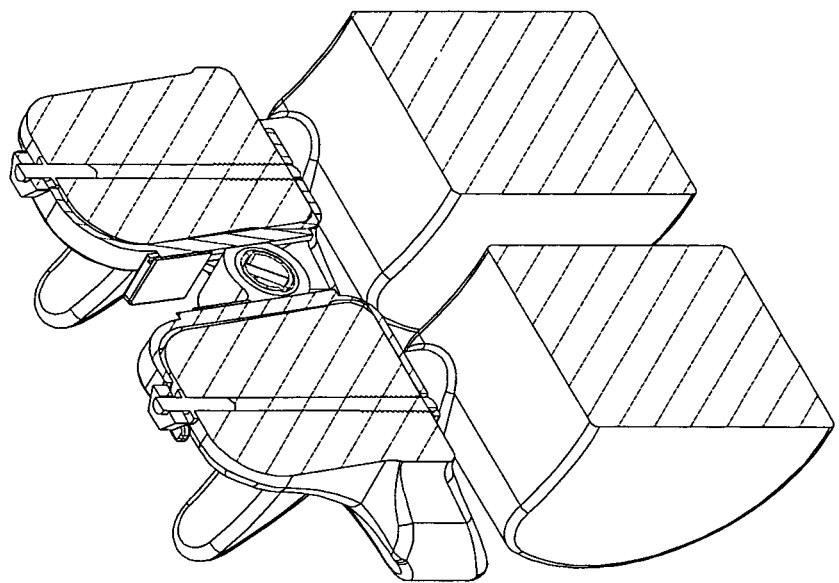
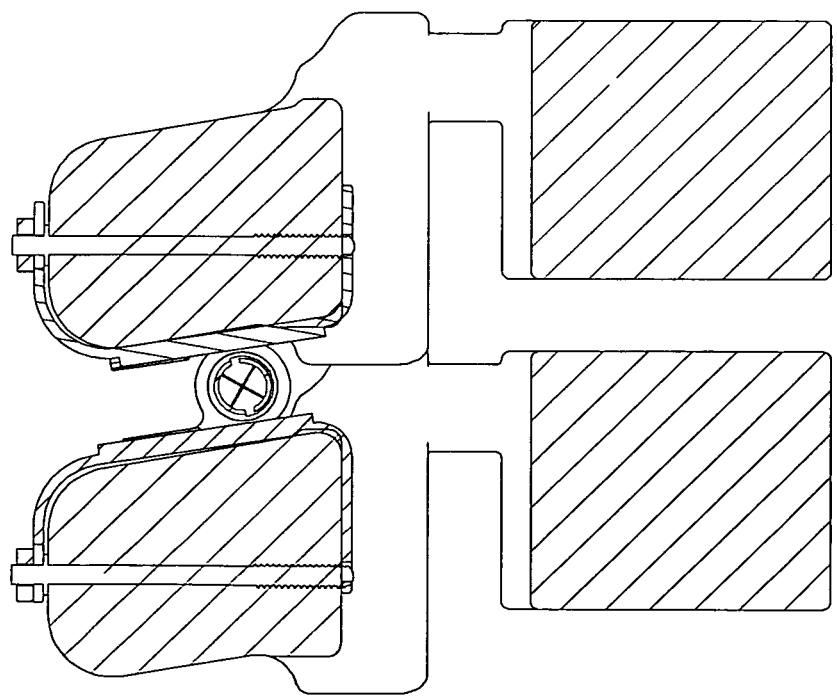
Fig. 21

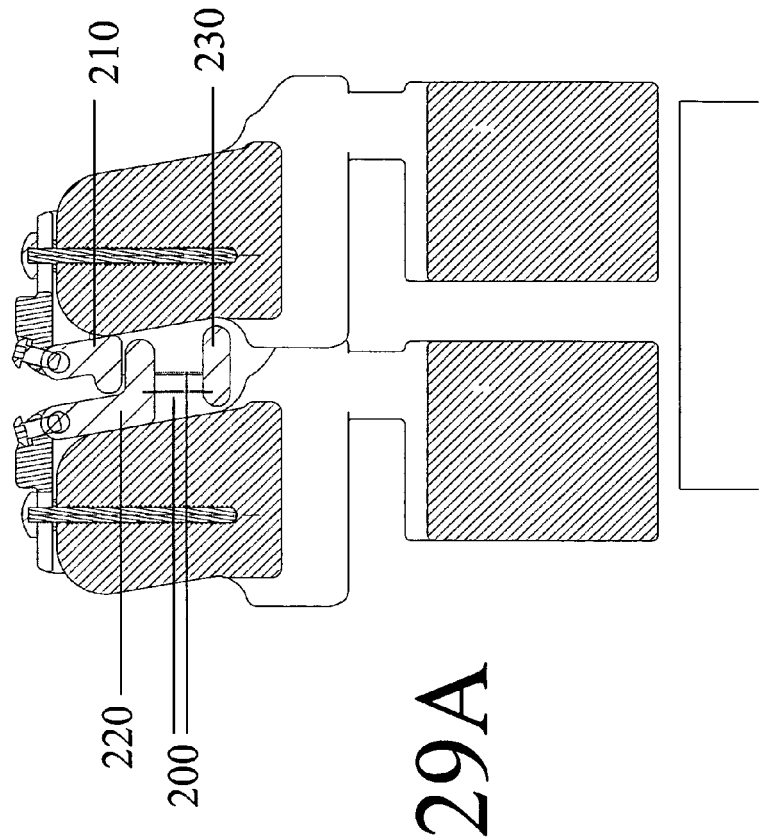
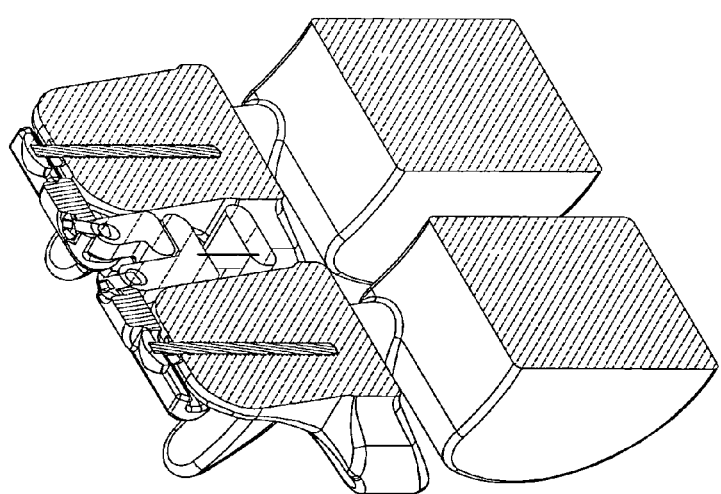
Fig. 29B
Fig. 29A

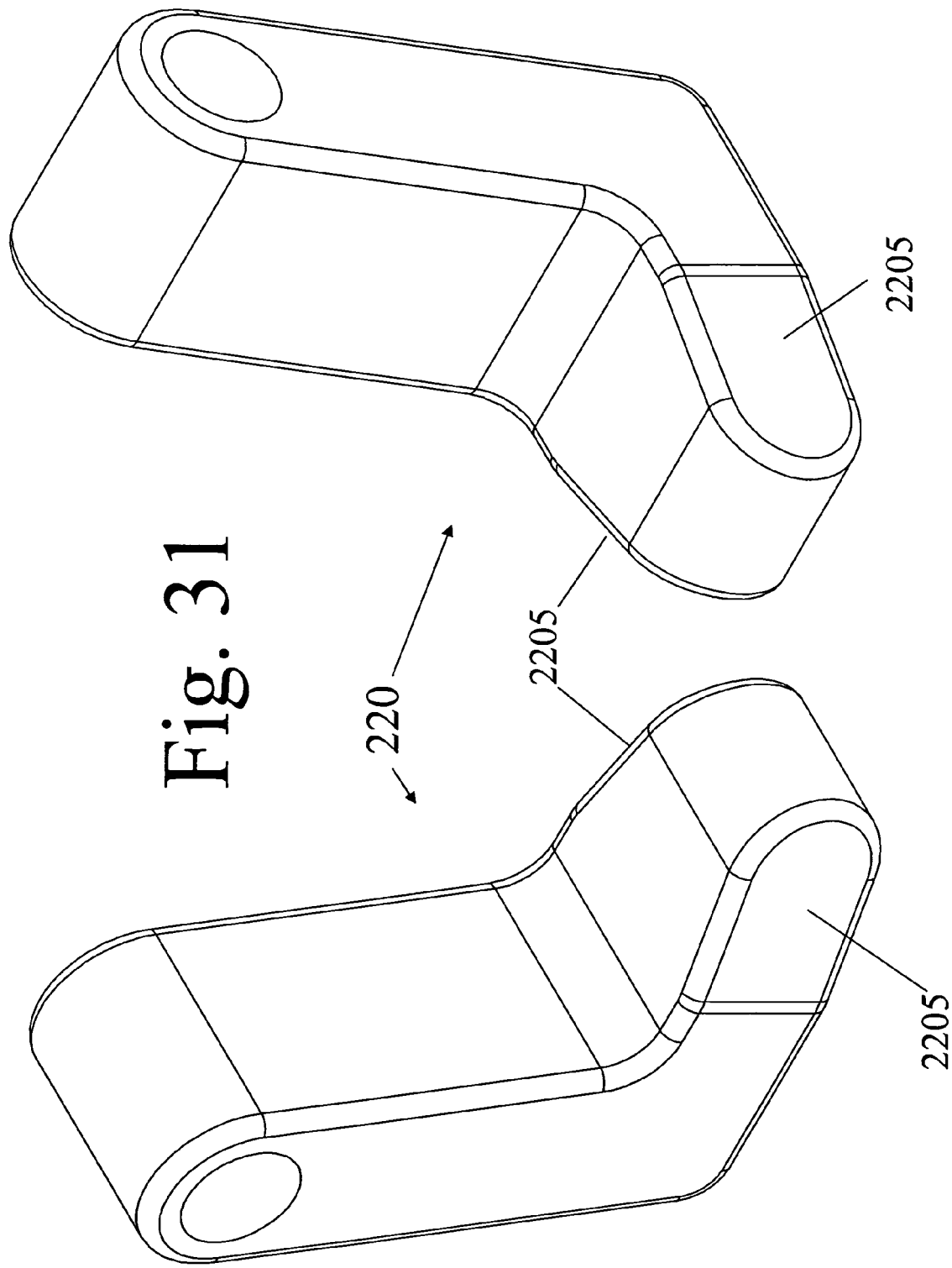

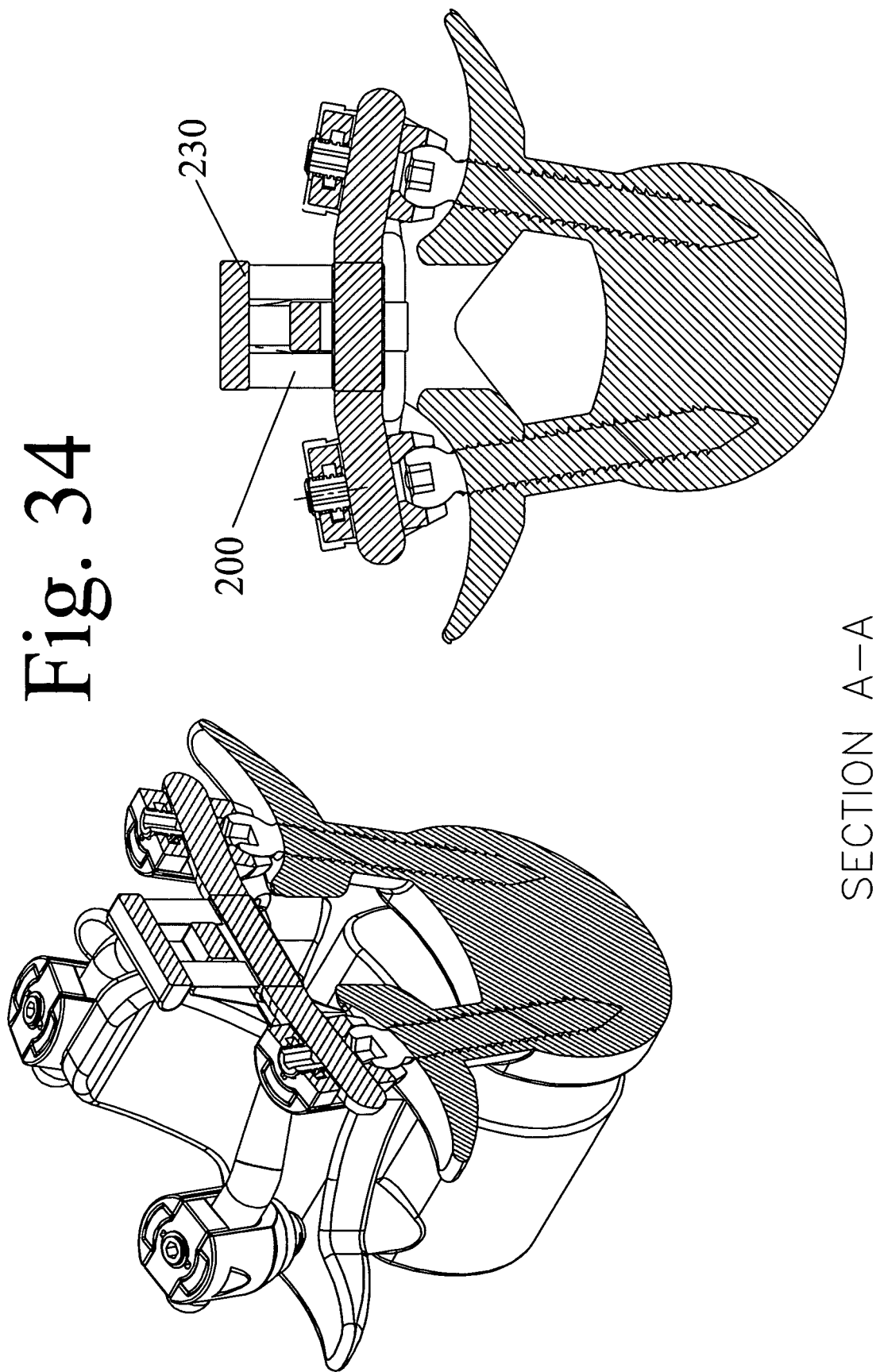

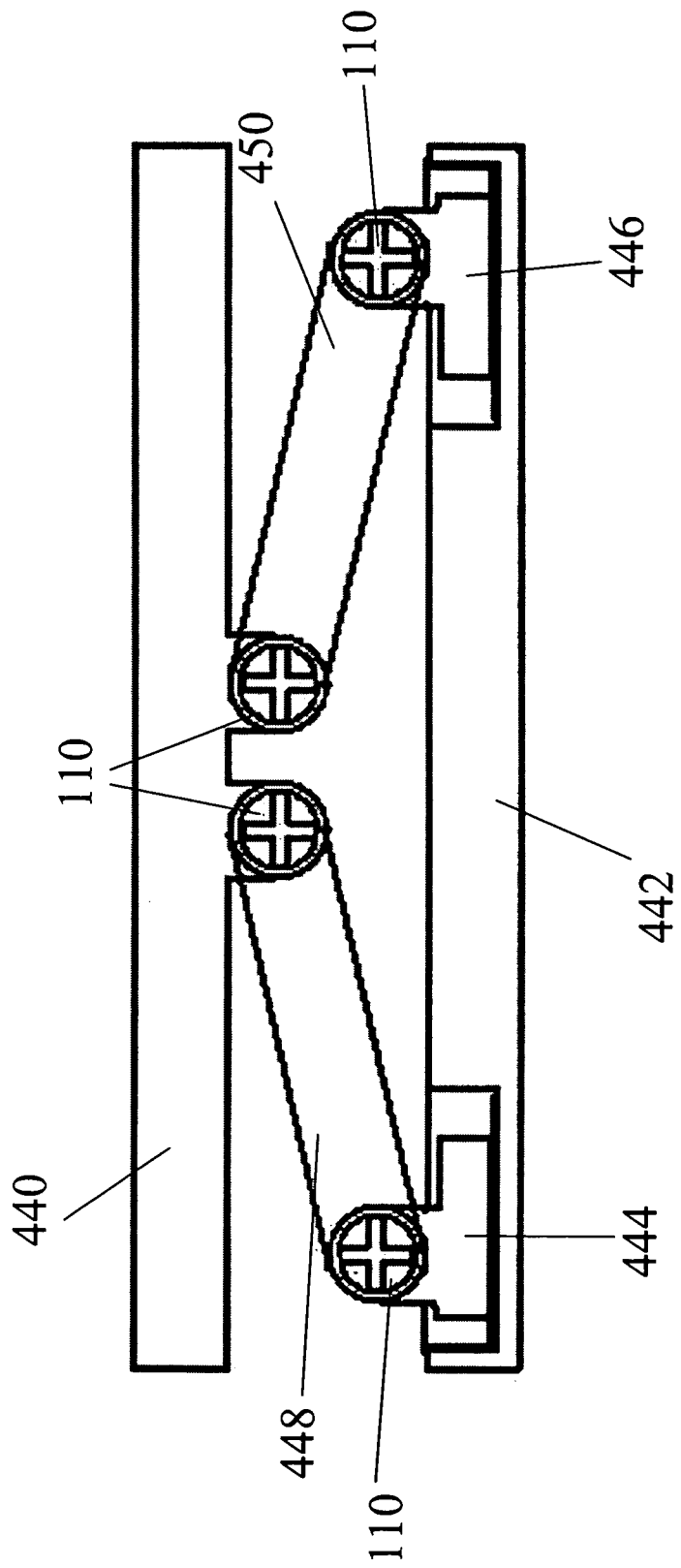

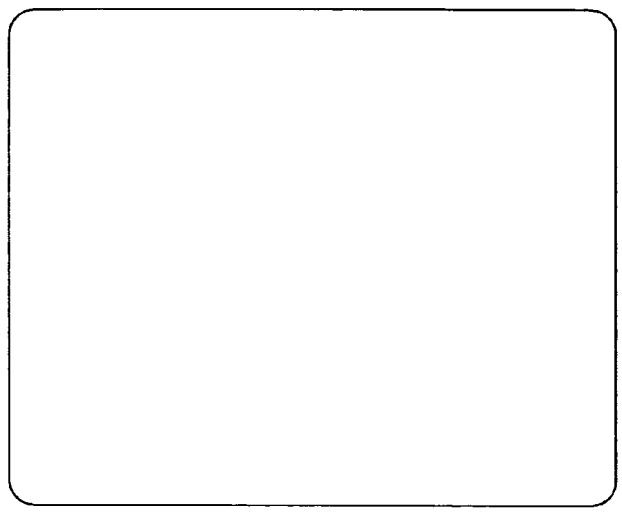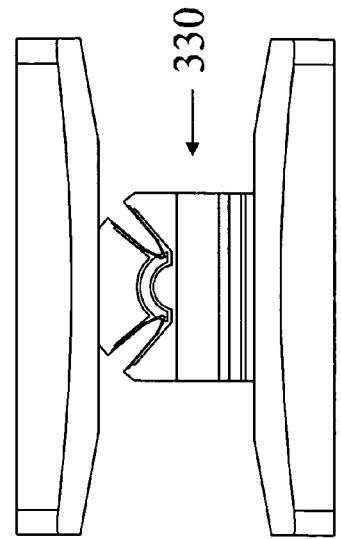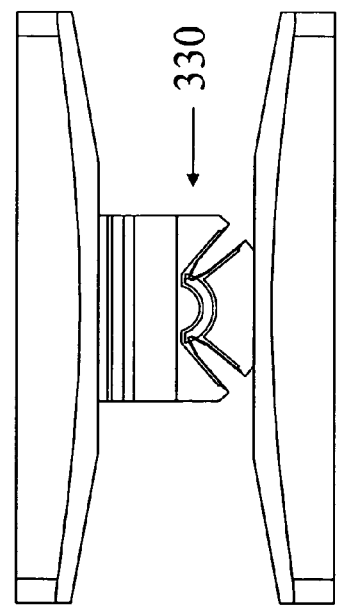
Fig. 38

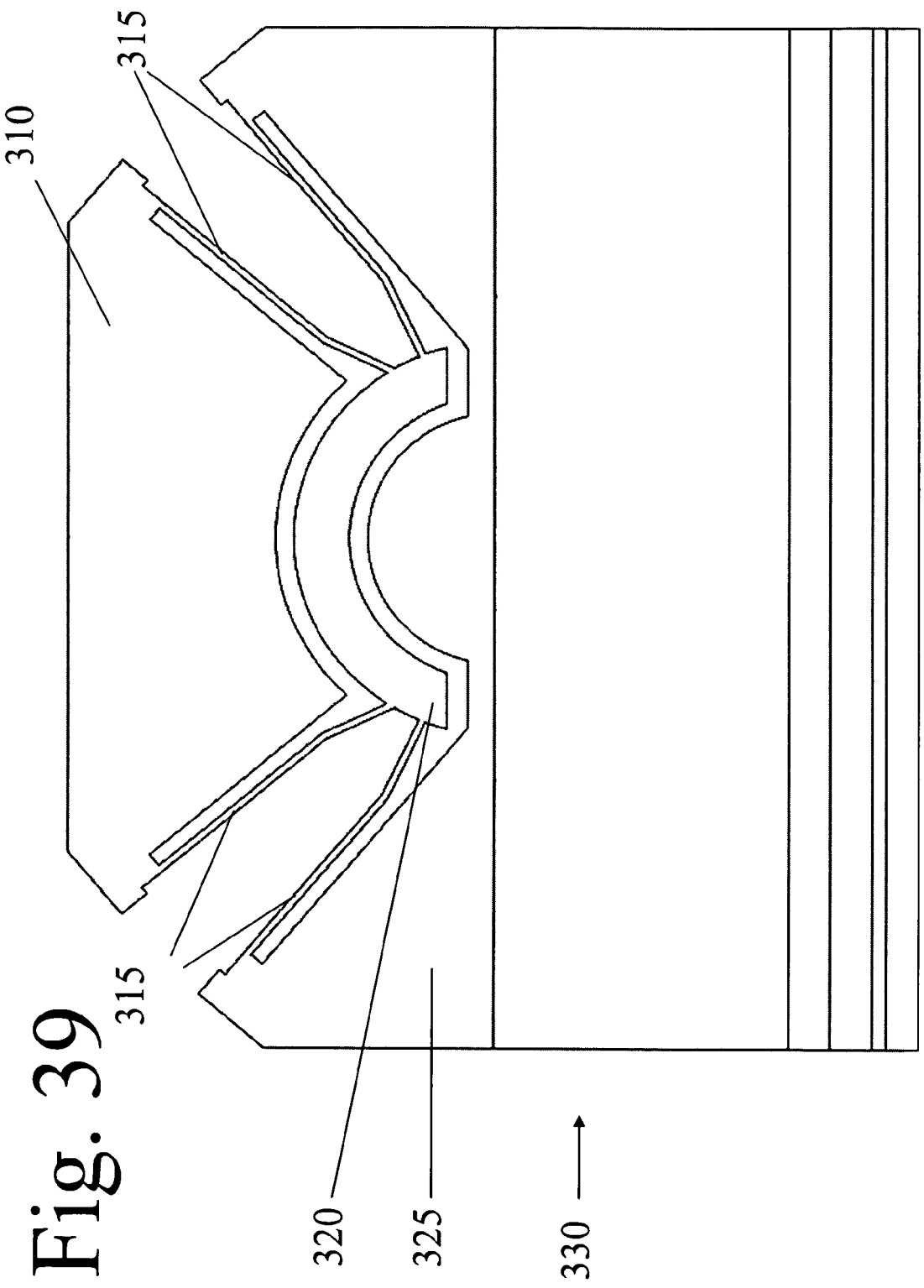

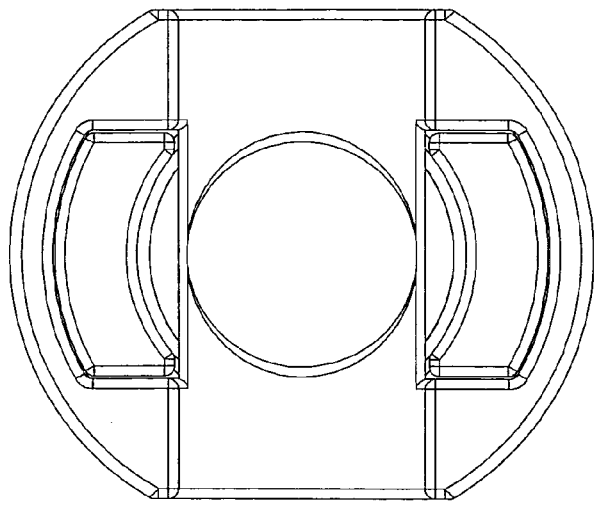
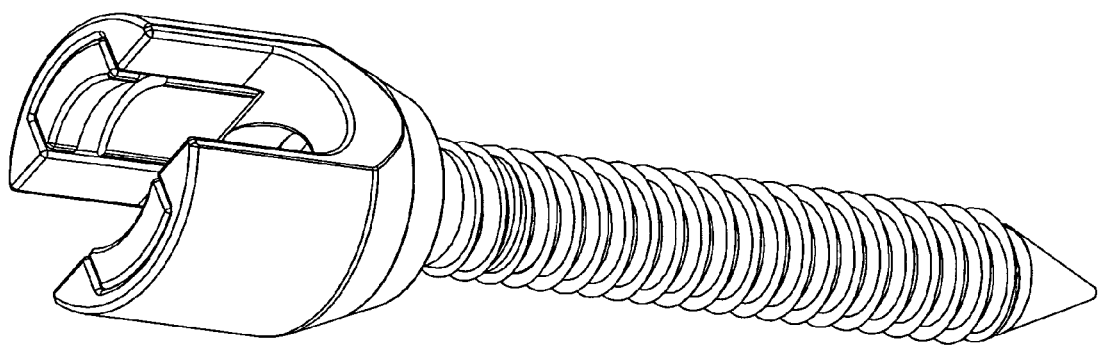
Fig. 43

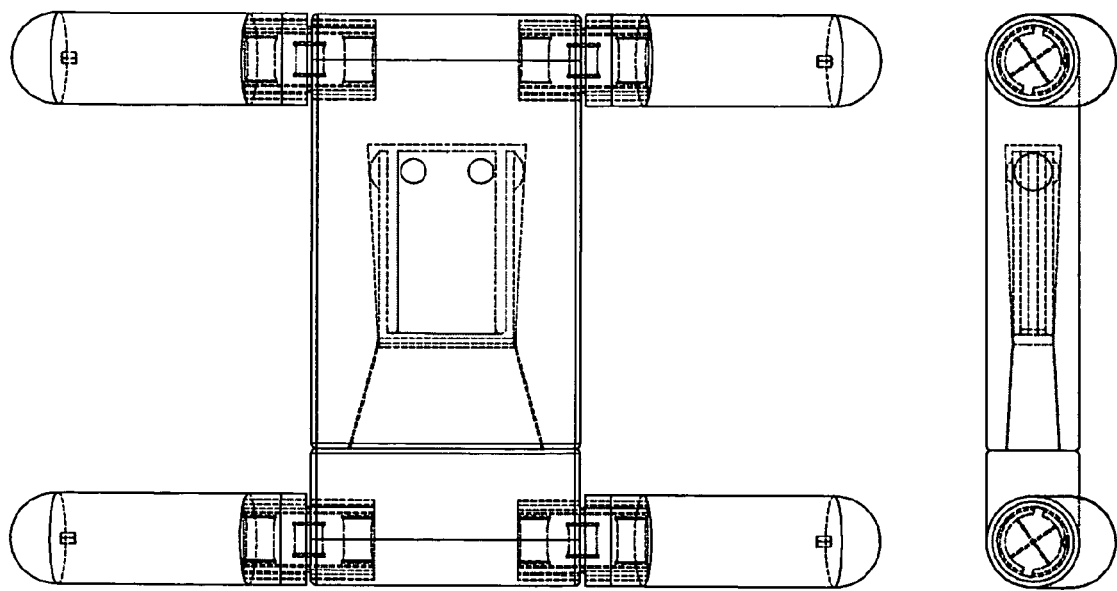
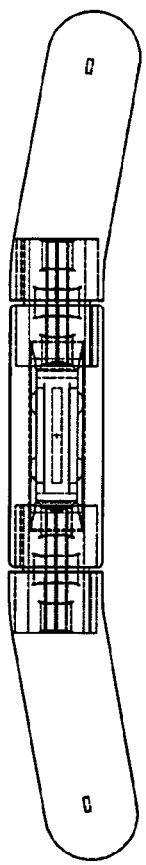
Fig. 48

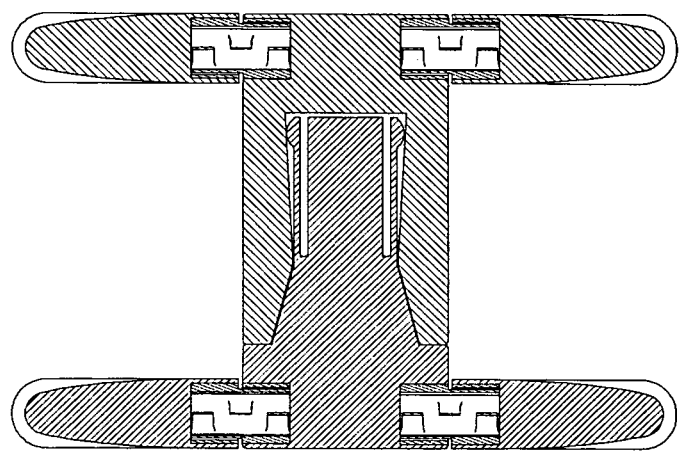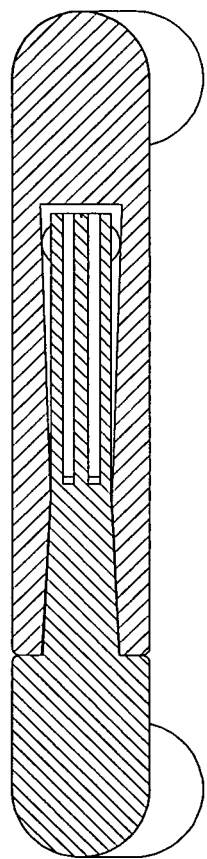
Fig. 49

DYNAMIC SPINAL STABILIZATION SYSTEMS AND METHODS OF USE

REFERENCE TO PRIORITY DOCUMENT

This application claims priority of U.S. Provisional Patent Application Ser. No. 60/874,195, filed Dec. 11, 2006. Priority of the aforementioned filing date is hereby claimed and the disclosures of the Provisional Patent Application is hereby incorporated by reference in its entirety.

BACKGROUND

The present disclosure relates to methods and devices that permit dynamic stabilization of the bony elements of the skeleton. The devices permit adjustment and maintenance of the spatial relationship(s) between neighboring bones. Depending on the specifics of the design, the motion between skeletal segments may be limited or enhanced in one or more planes.

Spinal degeneration is an unavoidable consequence of aging. The disability produced by the aging spine has emerged as a major health problem in the industrialized world. Alterations in the anatomical alignment and physiologic motion that normally exists between adjacent spinal vertebrae can cause significant pain, deformity, weakness, and catastrophic neurological dysfunction. The traditional surgical treatment of spinal disease is decompression of the neural elements and complete immobilization of the involved bony spinal segments. Over time, an extensive array of surgical techniques and implantable devices has been formulated to accomplish this goal.

The growing experience with spinal fusion has shed light on the long-term consequences of vertebral immobilization. It is now accepted that fusion of a specific spinal level will increase the load on, and the rate of degeneration of, the spinal segments immediately above and below the fused level. As the number of spinal fusion operations have increased, so have the number of patients who require extension of their fusion to the adjacent, degenerating levels. The second procedure necessitates re-dissection through the prior, scarred operative field and carries significantly greater risk than the initial procedure while providing a reduced probability of pain relief. Further, extension of the fusion will increase the load on the motion segments that now lie at either end of the fusion construct and will accelerate the rate of degeneration at those levels. Thus, spinal fusion begets additional fusion surgery.

In view of the proceeding, there is a growing recognition that segmental spinal fusion and complete immobilization is an inadequate solution to abnormal spinal motion and vertebral mal-alignment. Correction of the abnormal movement and preservation of spinal mobility is a more intuitive and rational treatment plan.

The vast experience gained in the implantation of mobile prostheses in the hip, knee, shoulder, ankle, digits and other joints of the extremities has shown that the wear debris produced by the bearing surfaces and the loosening that occur at the bone-device interface are major causes of implant failure. The latter is at least partially caused by the former, since it's been shown that the particulate debris from the bearing surfaces promote bone re-absorption at the bone-device interface and significantly accelerates device loosening. In the long term, the degradation products of the implant materials may also produce negative biological effects at distant tissues within the implant recipient.

While ceramic and polymer implant components produce wear debris, these degradation products are usually deposited as insoluble particles around the implant thereby limiting the extent of potential toxicity. In contrast, metallic degradation products may be present as particulate and corrosion debris as well as free metals ions, composite complexes, inorganic metal salts/oxides, colloidal organo-metallic complexes and other molecules that may be transported to distant body sites. In fact, studies have revealed chronic elevations in serum and urine cobalt and chromium level after prosthetic joint replacement. Given the known toxicity of titanium, cobalt, chromium, nickel, vanadium, molybdenum and other metals used in the manufacture of orthopedic implants, the tissue distribution and biologic activity of their degradation products is of considerable concern. Host toxicity may be produced directly by the reactive metallic moieties as well as by their alterations of the immune system, metabolic function, and their potential ability to cause cancer. These issues are thoroughly discussed in the text "Implant Wear in Total Joint replacement" edited by Thomas Wright and Stuart Goodman and published by the American Academy of Orthopedic Surgeons in 2000. The text is hereby incorporated by reference in its entirety.

Unlike joints in the extremities, proper function of the spinal joints (i.e., inter-vertebral disc and facet joints) returns the attached bones to the neutral position after the force producing the motion has dissipated. That is, a force applied to the hip, knee or other joints of the extremities produces movement in the joint and a change in the position of the attached bones. After the force has dissipated, the bones remain in the new position until a second force is applied to them. In contrast, the visco-elastic properties of the spinal disc and facet joint capsule dampen the force of movement and return the vertebral bones to a neutral position after the force acting upon them has dissipated.

Prosthetic joint implants that attempt to imitate native spinal motion have usually employed springs, polyurethane, rubber and the like to recreate the visco-elastic properties of the spinal joints. When subjected to the millions of cycles of repetitive loading that is required of a spinal joint prosthesis, all implants to date have been plagued by excessive wear and degeneration secondary to the fairly modest wear characteristics of these elastic elements. Thus, in addition to the wear debris generated by the bearing surface(s), the elastic materials used to dampen spinal motion will produce a second source of degradation products. Given the number of joints in the spine and the extensive potential application of replacement technology in these joints, it is critical that the wear debris from the implanted prosthesis be minimized.

SUMMARY

The preceding discussion illustrates a continued need in the art for the development of mobile prostheses with a reduced wear profile. This development would maximize the functional life of the prostheses and minimize the production of toxic degradation products.

In a first embodiment, a frictionless pivot member is used to inter-connect multiple links and produce a scissor jack-like device with minimal frictional wear characteristics. The device is attached to at least two vertebras, wherein a first device segment is attached to a first vertebra and at least one additional device segment is attached to at least one additional vertebra. The implanted device functions to control and dampen the movement between the attached vertebral bodies. Multiple methods of device attachment are shown.

In a second embodiment, the frictionless pivot member is used to manufacture an orthopedic device capable of at least partially replacing the function of a natural inter-vertebral disc. In a third embodiment, the frictionless pivot member is used to construct a connector that is used to inter-connect at least two bone screws that are connected to at least two vertebral bones. The inter-connector will function to control and dampen the movement between the attached vertebral bodies.

In other embodiments, devices are constructed out of malleable slats that are attached to the vertebral bodies in unique configurations. The devices control and dampen vertebral movement in one or more planes of motion. In a final embodiment, a device with a pyramidal articulation is used to inter-connect the vertebral bodies. The device is adapted to resist motion and dampen the movement between the attached vertebral bodies.

In one aspect, there is disclosed an implant adapted to dynamically stabilize two or more vertebral bodies, comprising: a first attachment member adapted to attach onto a first vertebral body; at least one second attachment member adapted to attach onto at least one additional vertebral body; at least one linkage member coupled to the attachment members; and at least one pivotable bearing mechanism that connects the linkage members and the attachment members, wherein: A) the pivotable bearing mechanism contains at least two rotatable members that pivot around a common central axis but do not directly contact one another; and B) the pivotable bearing mechanism contains at least one malleable member that connects the rotatable members and reversibly returns the bearing mechanism to a neutral position after the dissipation of a force acting upon it.

Other features and advantages will be apparent from the following description of various embodiments, which illustrate, by way of example, the principles of the disclosed devices and methods.

BRIEF DESCRIPTION OF THE DRAWINGS

FIG. 2 shows various views of the orthopedic implant attached to the vertebral bones.

FIG. 3A shows an assembled view of a portion of the implant.

FIG. 3B shows an exploded view of a portion of the implant.

FIG. 4 shows a perspective view of an embodiment of an articulation member.

FIG. 5 shows the articulation member in partial cross section.

FIG. 7A shows an embodiment of an articulating rod.

FIG. 7B shows the rod of FIG. 7A in cross-section.

FIGS. 9-14B show additional embodiments of orthopedic implants.

FIGS. 19-21 show another embodiment of an interspinous device.

FIGS. 29A and 29B show the device in cross-section.

FIG. 31 shows another embodiment of a flex member.

FIGS. 33 and 34 illustrate perspective and cross-sectional views of another embodiment of an interspinous device.

FIG. 35 illustrates a coronal section through an embodiment of a mobile implant device.

FIGS. 37-40B illustrate multiple embodiments of mobile devices that are placed within the disc space between two vertebral bodies and used to at least partially replace and/or augment the function of the native disc.

FIG. 43 shows an exemplary bone screw assembly.

FIGS. 46-49 show a dynamic rod assembly that includes two rod members that are movably attached to one another via a dynamic pyramidal connector.

DETAILED DESCRIPTION

Figure 1:
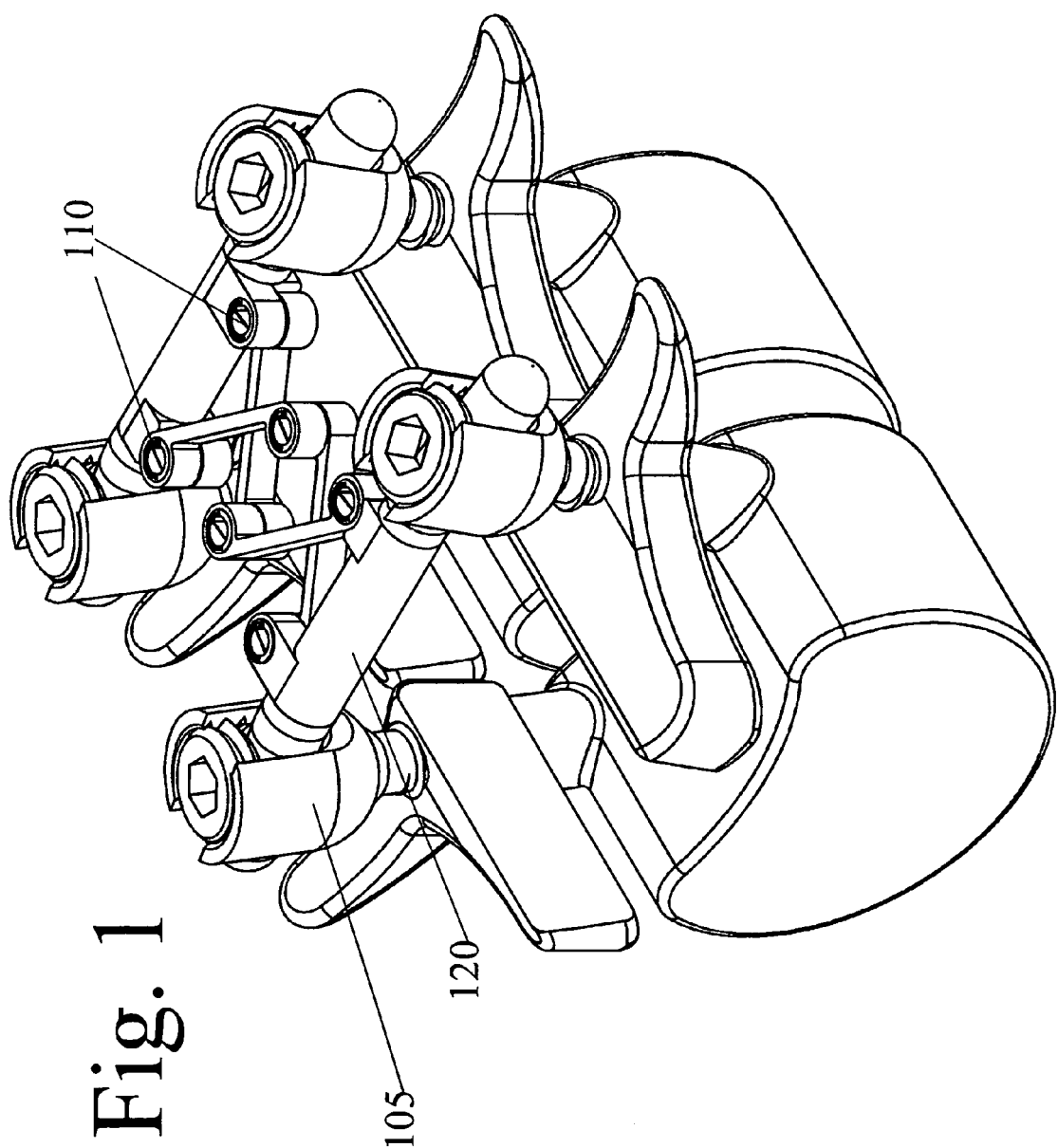
FIG. 1 shows perspective views of an exemplary embodiment of a dynamic orthopedic implant.

FIG. 1 shows perspective views of an exemplary embodiment of a dynamic orthopedic implant. The implant can be anchored across multiple levels of vertebral bones via one or more anchor devices, such as bone screw assemblies 105 that anchor into the vertebral bones. The configuration of the bone screw assemblies 105 can vary. In an embodiment, the bone screw assemblies are polyaxial bone screw assemblies each having a housing that can be locked to a bone screw. It should be appreciated that other types of bone screw assemblies can be used. FIG. 2 shows various views of the orthopedic implant attached to the vertebral bones. For clarity of illustration, the vertebral bones are represented schematically and those skilled in the art will appreciate that actual vertebral bones may include anatomical details not shown in FIG. 1.

With reference to FIGS. 1, 2, and 3 the implant includes a connecting mechanism 107 (FIG. 3A) that employs one or more articulating members 110 that provide an articulating connection between two or more rods 120 over multiple vertebral levels. The rods 120 are adapted to extend across the vertebral midline when the implant is positioned on the spine. Opposite ends of the rods 120 are attached to respective anchor devices 105. The articulating members 110 and the rods 120 are adapted to rotate around a central axis in response to the application of a rotational load. The connecting mechanism 107 can be fixedly attached to one or both of the rods 120 such that the entire device is a unitary device. Alternately, the connecting mechanism 107 can modularly attach to one or both of the rods 120, as described more fully below. Moreover, the rods 120 can be articulating or can be solid rods of fixed size and shape, as described more fully below.

FIG. 3A shows an assembled view of the implant while FIG. 3B shows an exploded view of the implant. The connecting mechanism 107 includes the articulating members 110 that are interconnected via elongate link members 305. The link members 305 can move relative to one another as a result of articulation of the articulating members 110. In this regard, the articulating members 305 are adapted to provide frictionless or near frictionless movement about an axis of rotation, such as the axis of rotation A show in FIG. 3A. The axis of rotation extends through a central, longitudinal axis of the articulation member. In the embodiment shown in FIGS. 3A and 3B, the rods 120 are elongated sleeves that are adapted to receive an elongated rod therein. It should be appreciated that the rods 120 can be solid rods, sleeves, articulating rods, etc. In addition, the rods 120 can be replaced with another implant device other than a rod.

Figure 6:
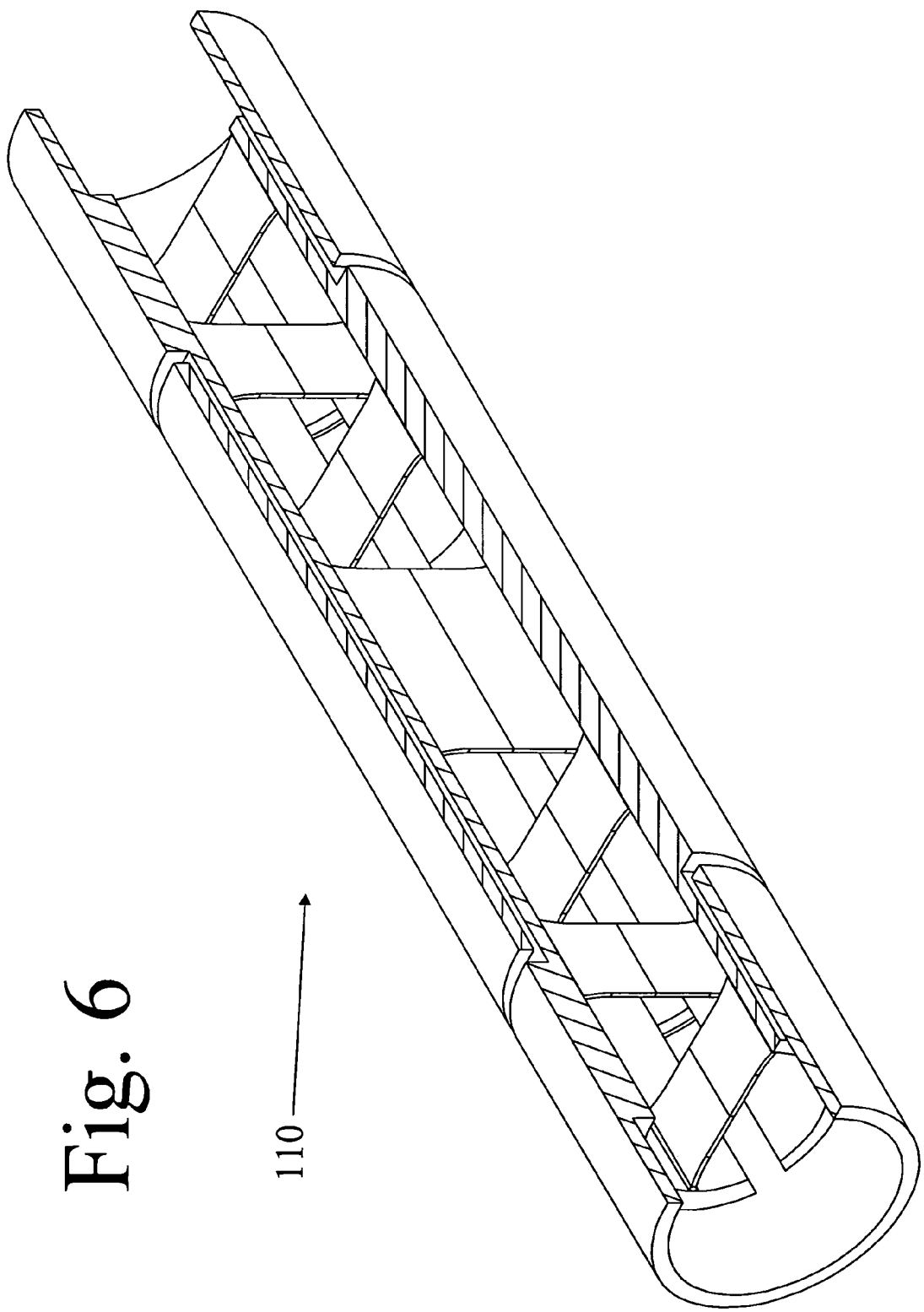
FIG. 6 shows another embodiment of an articulating member.

FIG. 4 shows a perspective view of an embodiment of an articulation member 110. FIG. 5 shows the articulation member 110 in partial cross section. With reference to FIGS. 4 and 5, each of the articulating members 110 is formed of a plurality of sections 410 and 420. The articulating member 110 permits the attached link members 305 (FIG. 3A) to rotate about the longitudinal axis of the articulating member. In one embodiment, the rotational range is +30 to −30 degrees, although it should be appreciated that the rang can vary. The articulating member 110 is a flexure based bearing, utilizing internal flexible slats 1110 contained within a cylindrical housing, to provide precise rotation with low hysteresis and no frictional losses. The bearing is stiction-free, requires no lubrication, and is self-returning. The articulating member can resist rotational movement away from a neutral state and the extent of resistance to rotation is directly related to the extent of rotation. The extent of resistance to rotation can be a pre-determined property of the device. In one embodiment, the articulation member is has high radial stiffness, high axial stiffness and is frictionless (hence, no particle wear debris). An exemplary articulating member of the type shown in FIGS. 4 and 5 is distributed by Riverhawk Company of New York under the name FREE FLEX PIVOT. FIG. 6 shows another embodiment of an articulating member 110. The embodiment of FIG. 6 comprises several sections formed of a plurality of internal, interconnected structures that are adapted to move and/or deform relative to one another.

Figure 8:
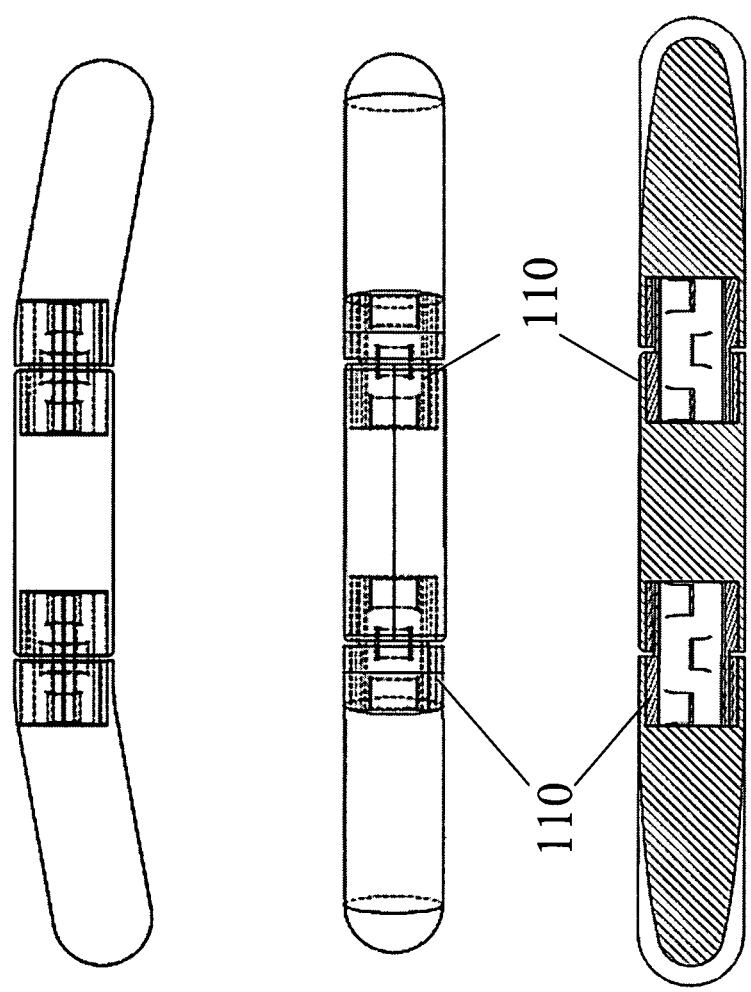
FIG. 8 shows another embodiment of an articulating rod.

As mentioned, the rod 120 can be a solid device of fixed shape or it can be an articulating device adapted to change shape in response to loads. FIG. 7A shows an embodiment of an articulating rod 120 formed of interconnected rod sections including an articulating member 705 that is constructed in a manner similar to the articulating member 110. The articulating member 705 permits the rod sections to rotate about the axes of the central articulating member 705. FIG. 7B shows a cross-sectional view of the articulating member 705, which comprises several sections formed of a plurality of internal slats that are adapted to deform in response to the rotational movement of central member 705 relative to ends 706. FIG. 8 illustrates an alternative embodiment of an articulating rod. The rod contains three solid segments that contain end recesses adapted to accept an articulation member 110. In the assembled state, a first articulation member 110 provides rotational movement between the first and second rod segments and a second articulation member 110 provides rotational movement between the second and third rod segments.

Figure 10:
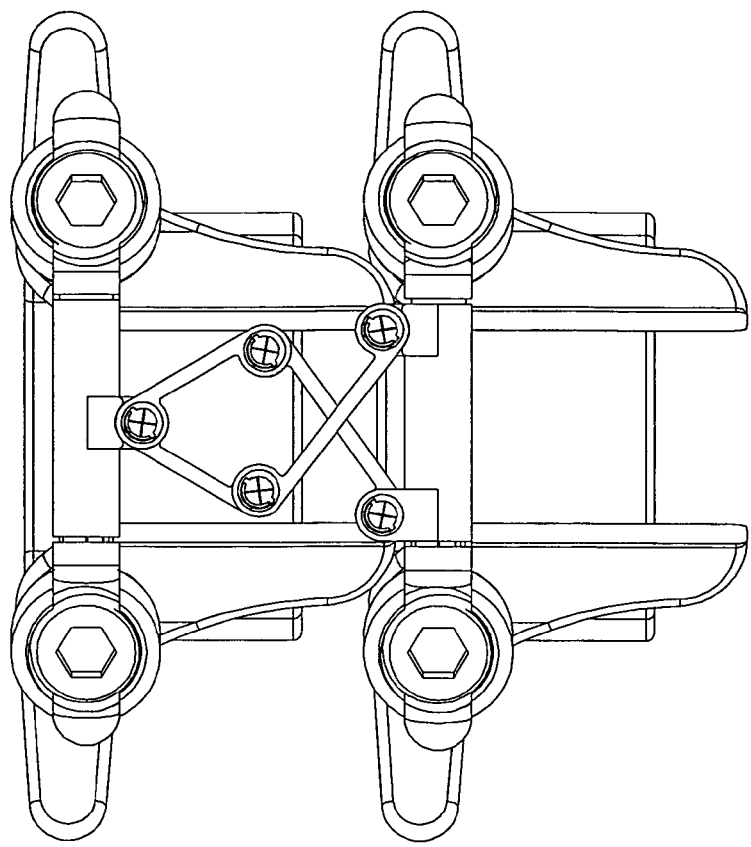
Figure 9:
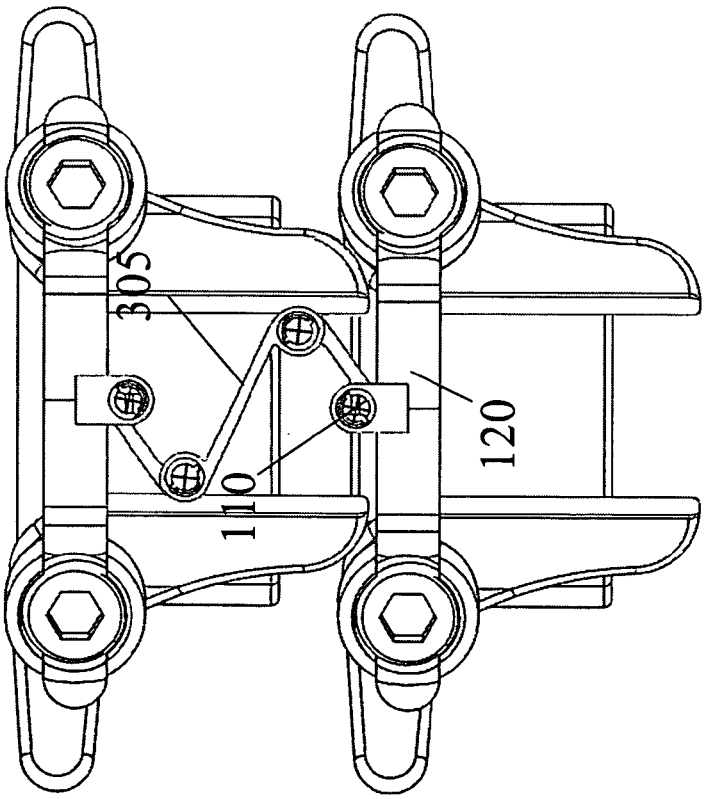

The implant can use various configurations of the connecting mechanism 107. The connecting mechanism can employ various quantities of articulating members 110 that are linked to one another via link members 305 arranged in various structural and geometric configurations. FIG. 9 shows an embodiment that includes several articulating members 110 that are linked together in series via several link members 305. The articulating members 110 are arranged in an undulating pattern between a pair of rods 120. FIG. 10 shows another embodiment of an implant. In this embodiment, one of the rods 120 is directly connected to two articulating members 110 while the opposite rod 120 has a direct connection to a single articulating member 110. A pair of in-between articulating members 110 are linked by link members 305 that cross over one another.

Figure 12:
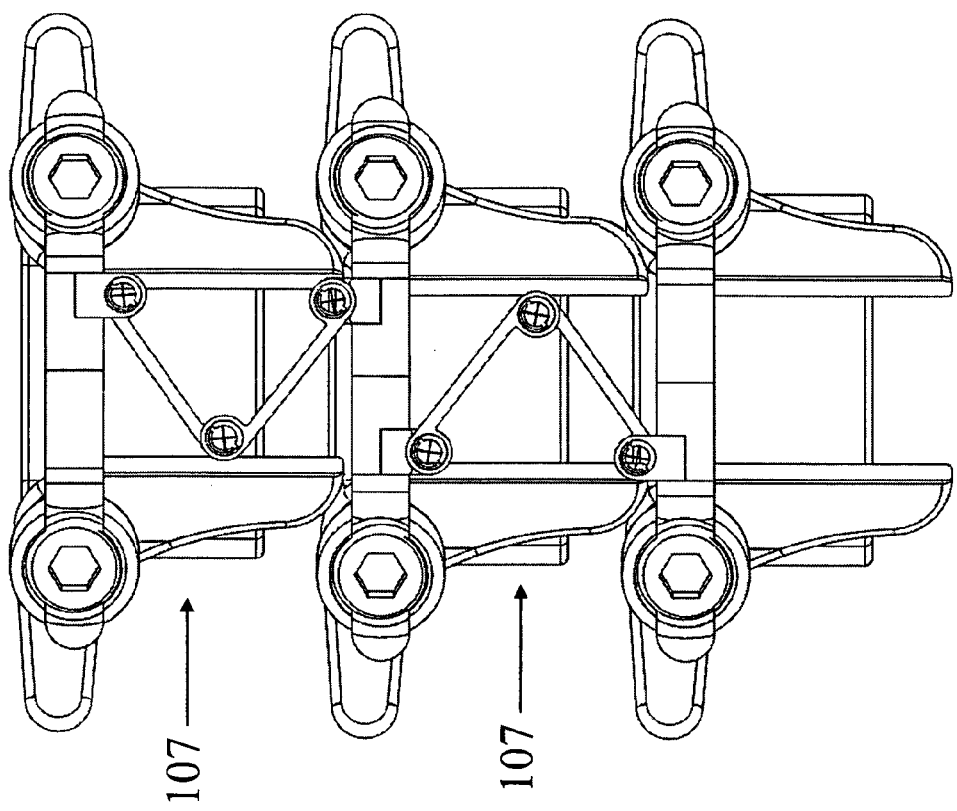
Figure 11:
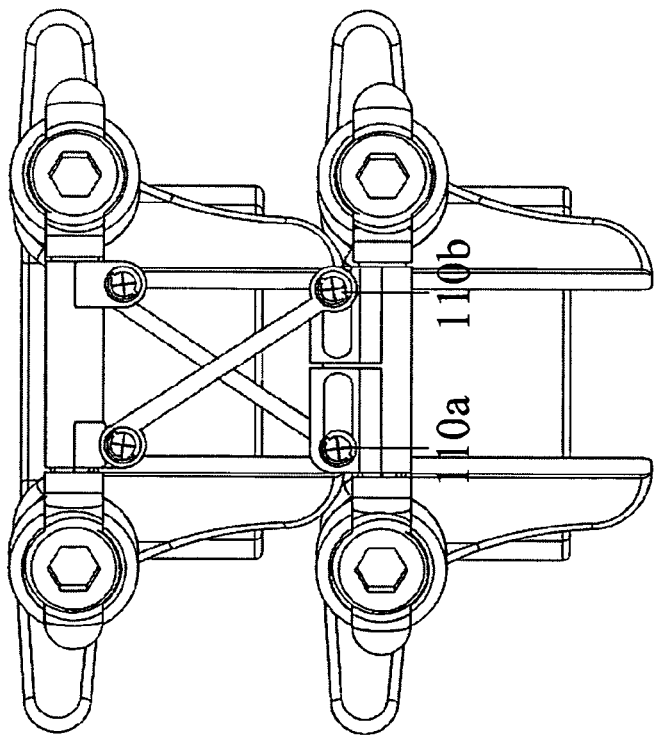

FIG. 11 shows another embodiment of an implant wherein four articulating members 110 are interlinked by link members 305 arranged in a cross-wise fashion. The articulating members 110a and 110b are slidably positioned in slots to permit sliding translation of the articulating members 110a and 110b within the slots and relative to the rod 120a. The implants can have several connecting mechanisms 107 that each extend across one or more vertebral levels. For example, FIGS. 12 and 13 shows an implant with two connecting mechanisms 107 that each extend across a vertebral level. The geometric arrangement of the linking arms and the articulating members can be the same between different levels or it can vary between levels.

Figure 14B:
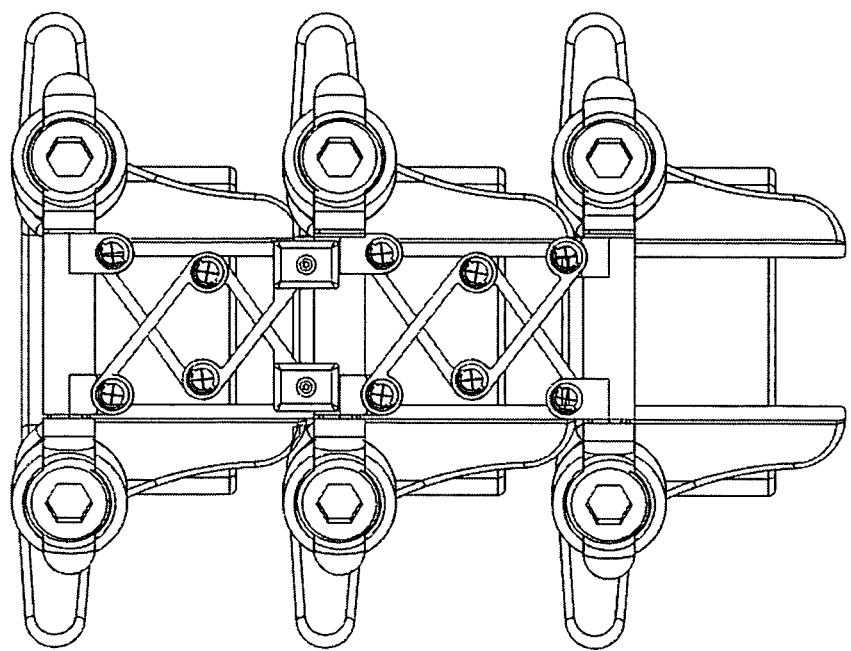
Figure 14A:
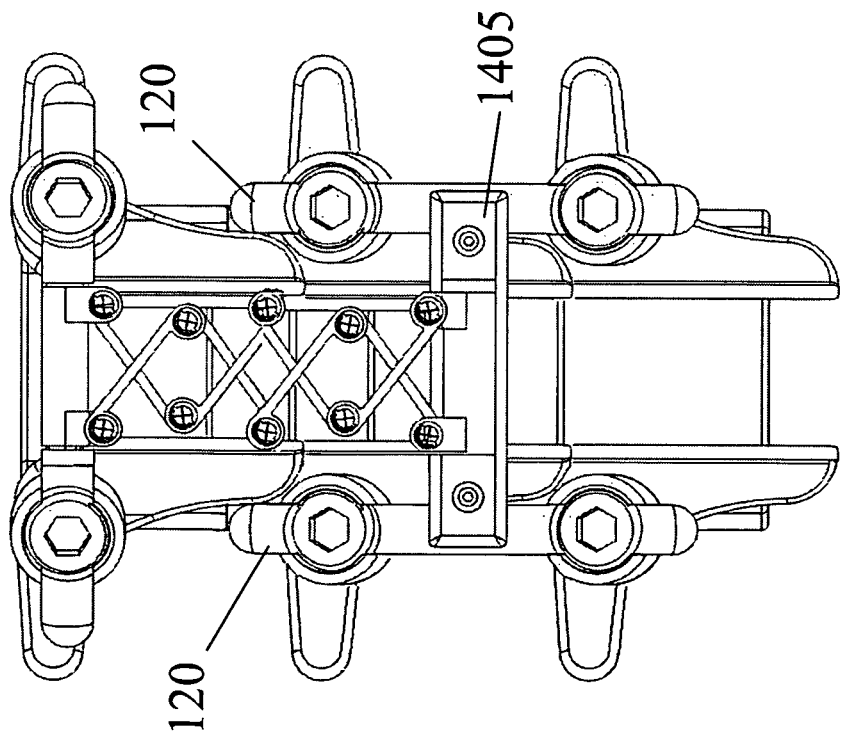

In certain circumstances, it may be desirable to provide one or more rods 120 that extend parallel to the vertebral midline. FIG. 14A shows an embodiment of an implant with rods 120 that are parallel to the vertebral midline along opposite sides of the vertebral midline. The implant also includes a cross-member 1405 that extends across the vertebral midline and connects at opposite ends to the rods 120.

Figure 15B:
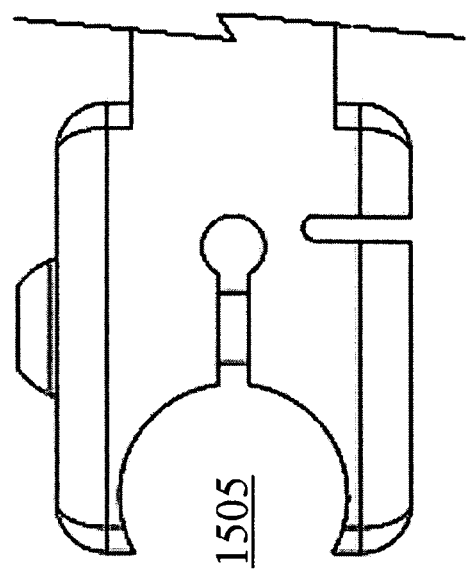
FIGS. 15A and 15B show modular attachment members.
Figure 15A:
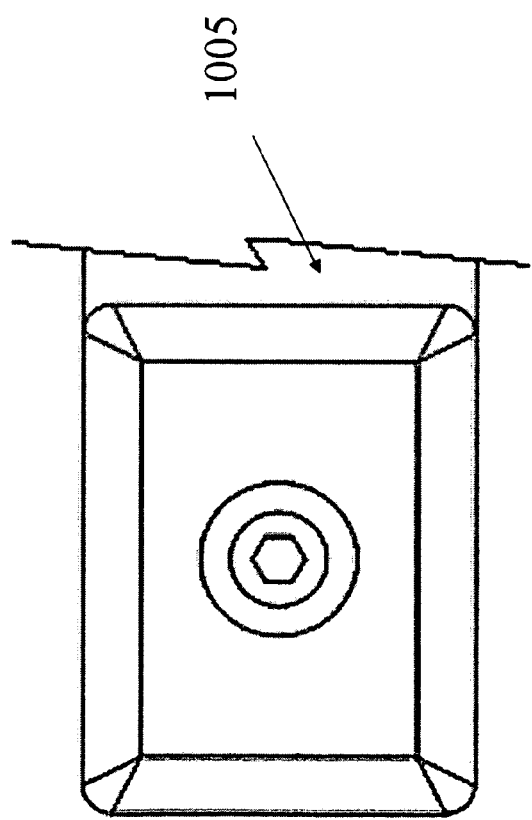

As mentioned, an embodiment of the connecting mechanism 107 is adapted to modularly attach to a rod 120 or to another device. This permits multiple connecting mechanisms to be removably attached to one another over several vertebral levels. For example, the embodiment of FIG. 10 has at least one modular attachment member 1005 that removably attaches to a rod 120 or to another type of device. The modular attachment member 1005 can be configured to removably attach to a rod or another type of device using various mechanisms. FIGS. 15A and 15B show top and side views of an embodiment of the attachment member 1005. The attachment member 1005 has a receiving cavity 1505 that is sized and shaped to removably receive a rod 120. It should be appreciated that the attachment member 1005 can have various types of structures that are adapted to removably receive or mate with a rod or other device.

Spinous Process Devices

Figure 16:
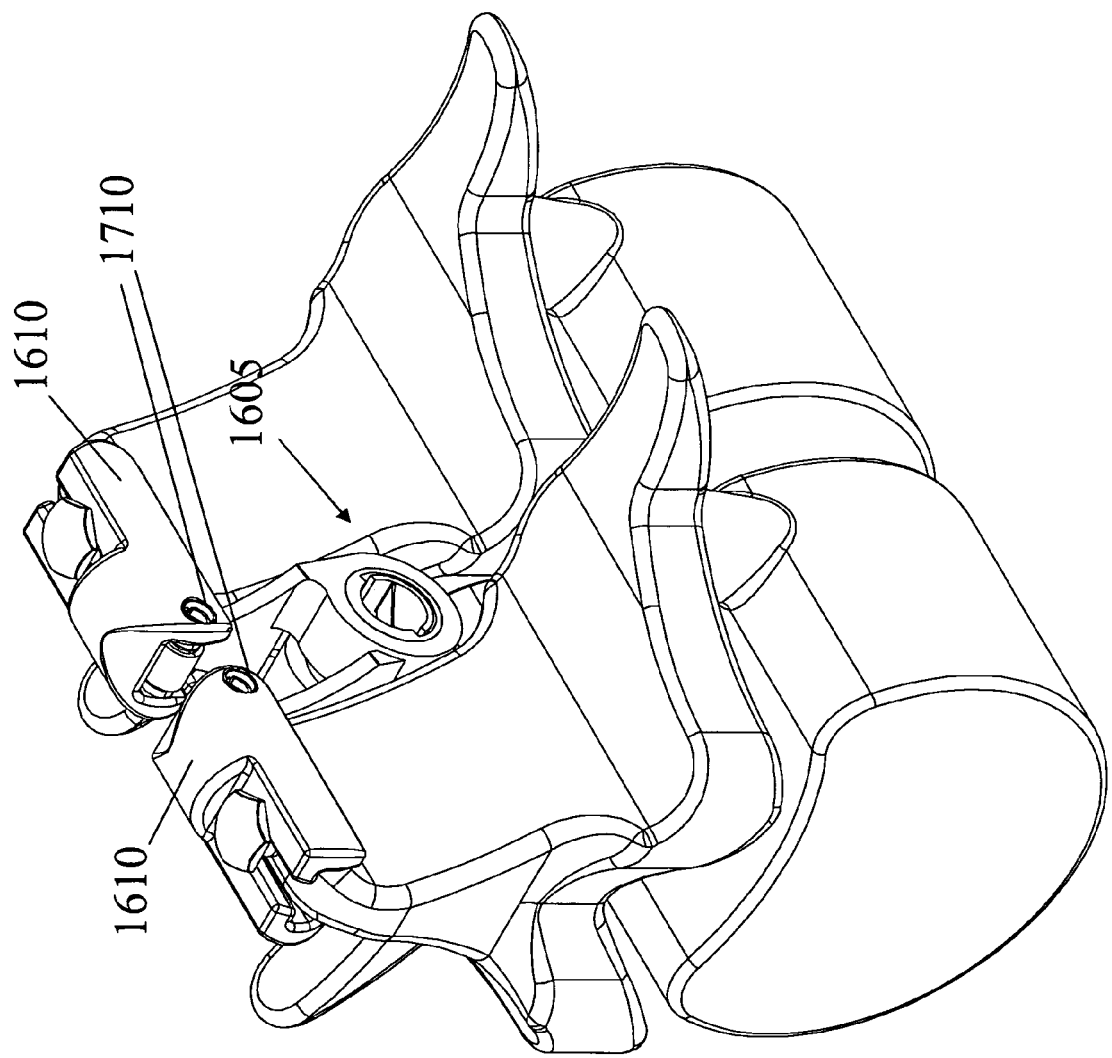
FIG. 16 shows a perspective view of an interspinous device that is configured for placement between the spinous processes of two adjacent vertebral bones.
Figure 17:
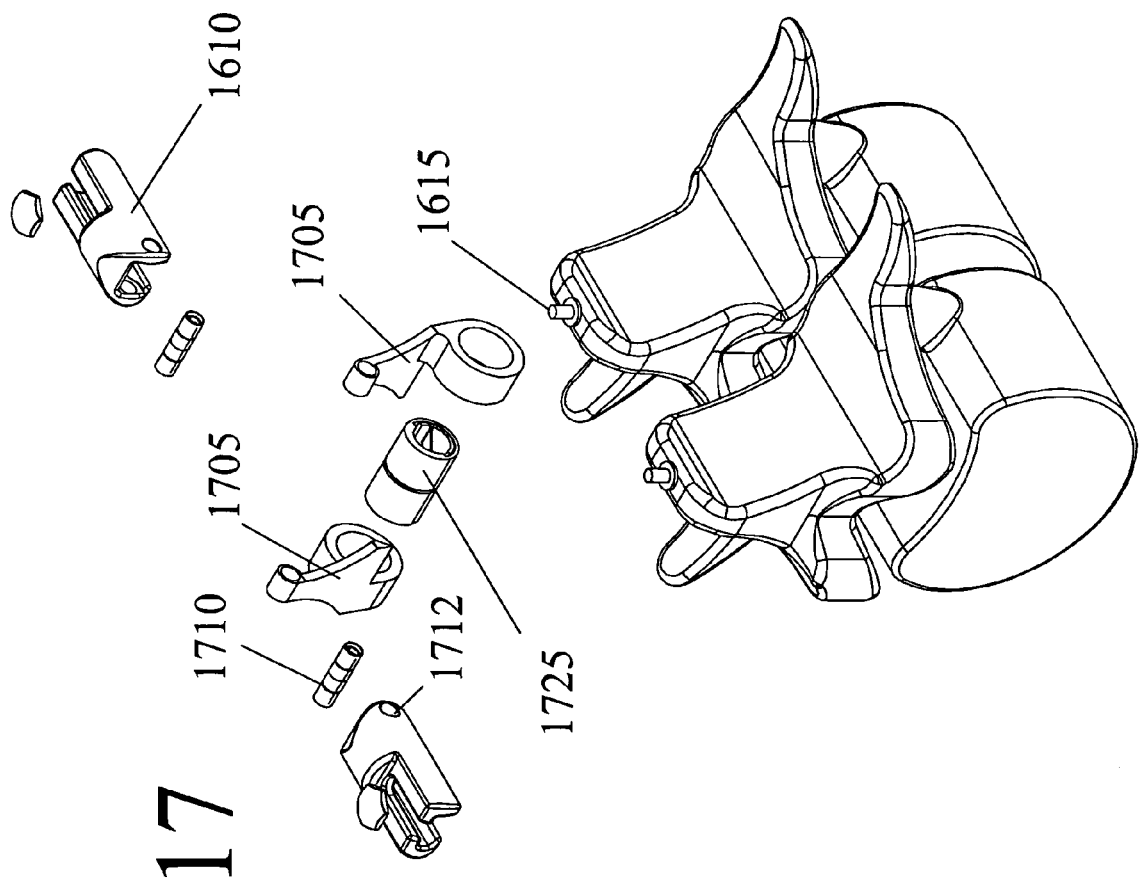
FIG. 17 shows an exploded view of the device of FIG. 16.
Figure 18:
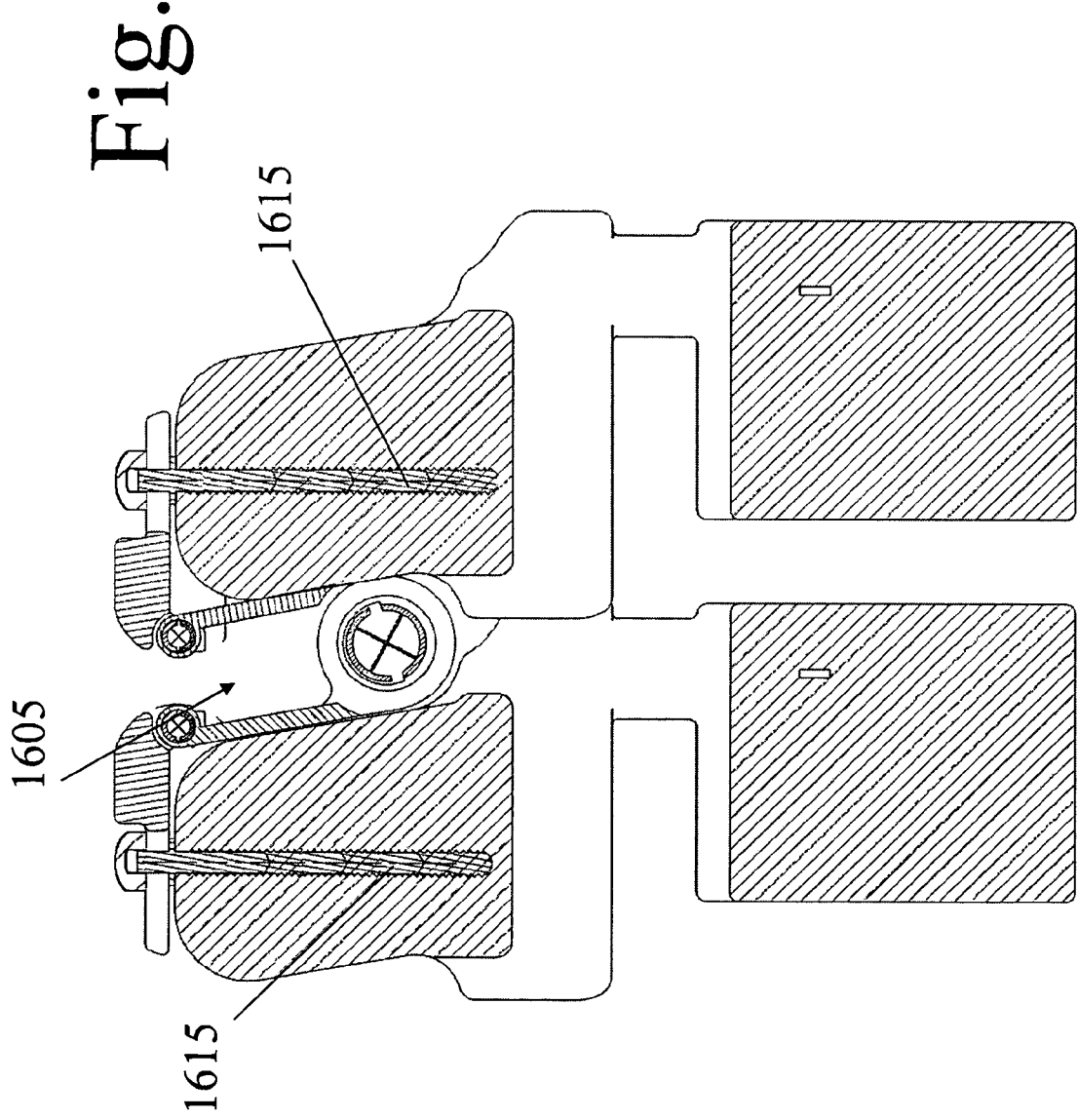
FIG. 18 shows a cross-sectional view of the device implanted on the vertebral bones.

FIGS. 16-26 show various flexible pivoting interspinous devices that can be attached onto the spinous processes and/or lamina of neighboring vertebral bones. FIG. 16 shows a perspective view of an interspinous device that is configured for placement between the spinous processes of two adjacent vertebral bones. FIG. 17 shows an exploded view of the device of FIG. 16. FIG. 18 shows a cross-sectional view of the device implanted on the vertebral bones. The device includes an articulating central region 1605 that is sized and shaped to fit between the spinous processes of the two adjacent vertebral bodies. The device further includes a pair of attachment regions 1610 each adapted to attach and anchor onto the spinous process of a vertebral body. The central region 1605 can have a variety of shapes and sizes for placement between the spinous processes. The attachment regions 1610 can also have various sizes and shapes for attachment to the spinous processes.

The attachment regions are attached to a pair of threaded screws 1615 (threads not shown) that are attached the spinous processes. As shown in FIG. 18, the screws 1615 have shank regions that extend into the spinous processes. It should be appreciated that means other than screws can be used to attach the attachment regions to the spinous processes. The central region 1605 of the device limits the extent of vertebral extension at the implanted level. The malleable nature of the device resists vertebral extension and rotation. The device also resists anterior or posterior displacement of one vertebral level relative to the other. While the illustrated embodiment will permit anterior flexion alone, additional members 110 may be added in the desired plane to produce additional rotational planes.

With reference to the exploded view of FIG. 17, the central region 1605 includes a pair of arms 1705 that are movably attached to articulation locations or articulation points 1710. The articulation points 1710 provide means of movement of the arms 1705 about the articulation points. The articulation points 1710 can be conventional pins that serve as hinges, or the articulation points can be articulation members of the type shown in FIGS. 5-6. The articulation points 1710 are cylindrically shaped and rotatably positioned in openings 1712 in the attachment regions 1610 and in the arms 1705 to provide rotational movement therebetween. The arms 1705 are attached to a housing 1720 having an opening that receives a flexible pivot member 1725 that has a construction similar to or the same as the articulation members shown in FIGS. 5-6. The pivot member 1725 serves as a central flexible pivot between the spinous processes. When implanted as shown in FIGS. 16 and 18, the device allows vertebral movement in certain planes while limiting vertebral motion.

Figure 19:
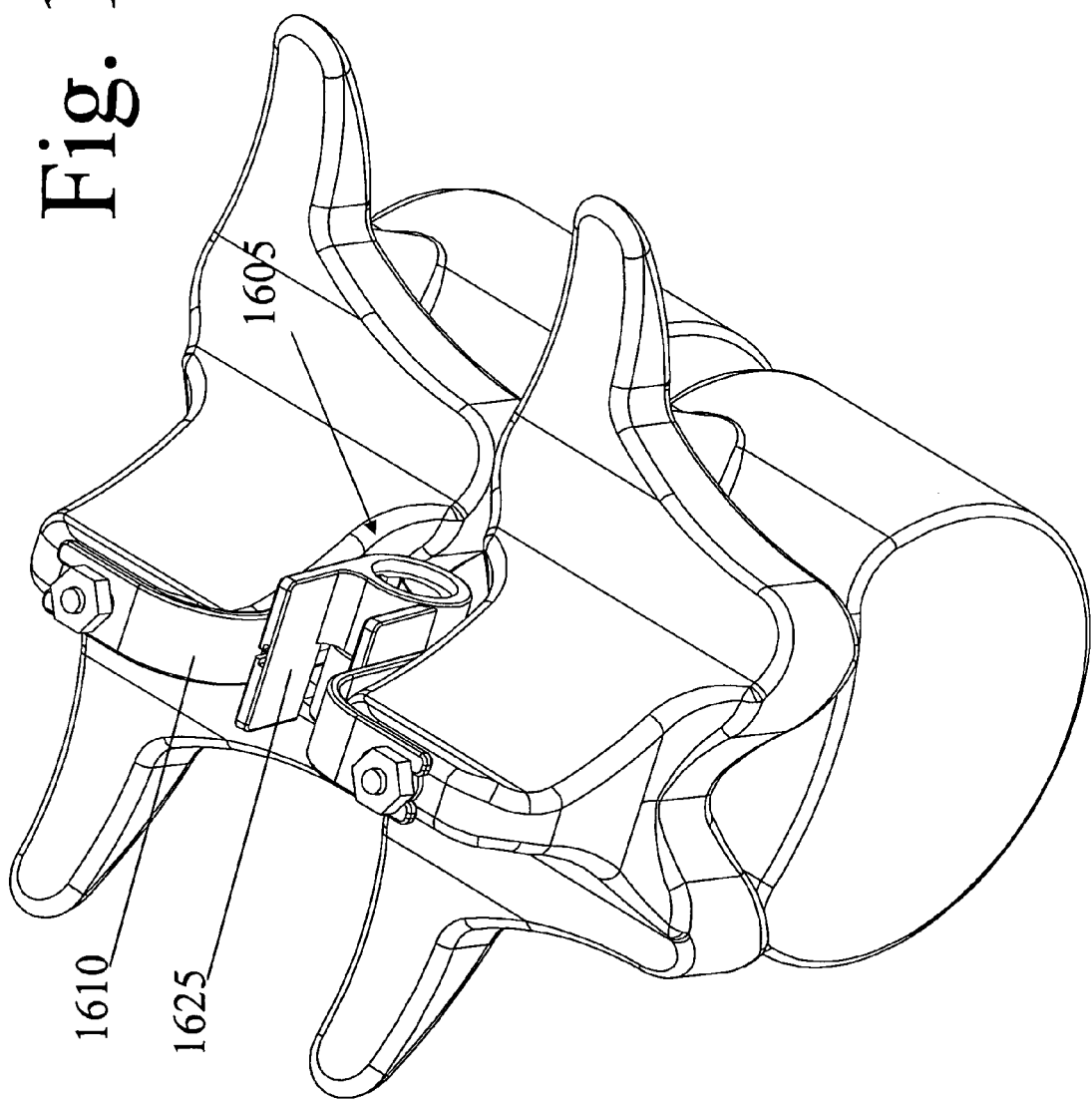
Figure 20:
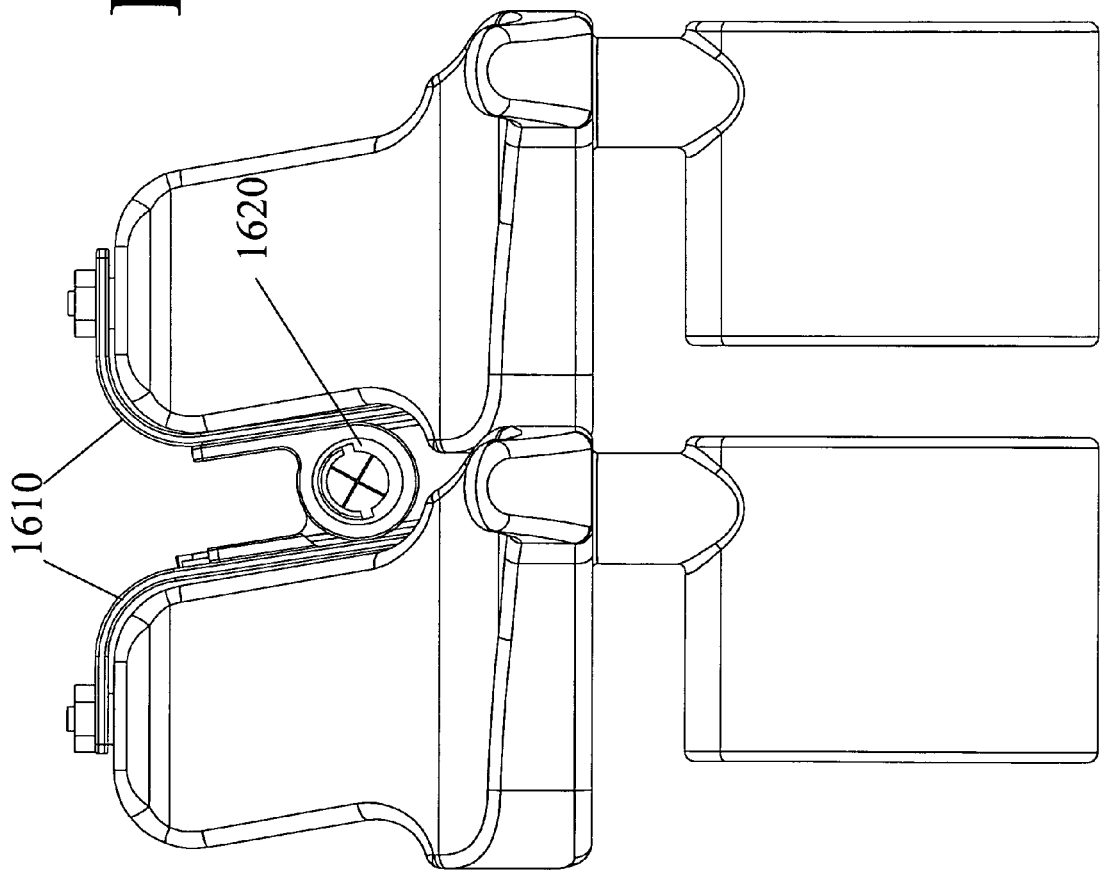
Figure 22:
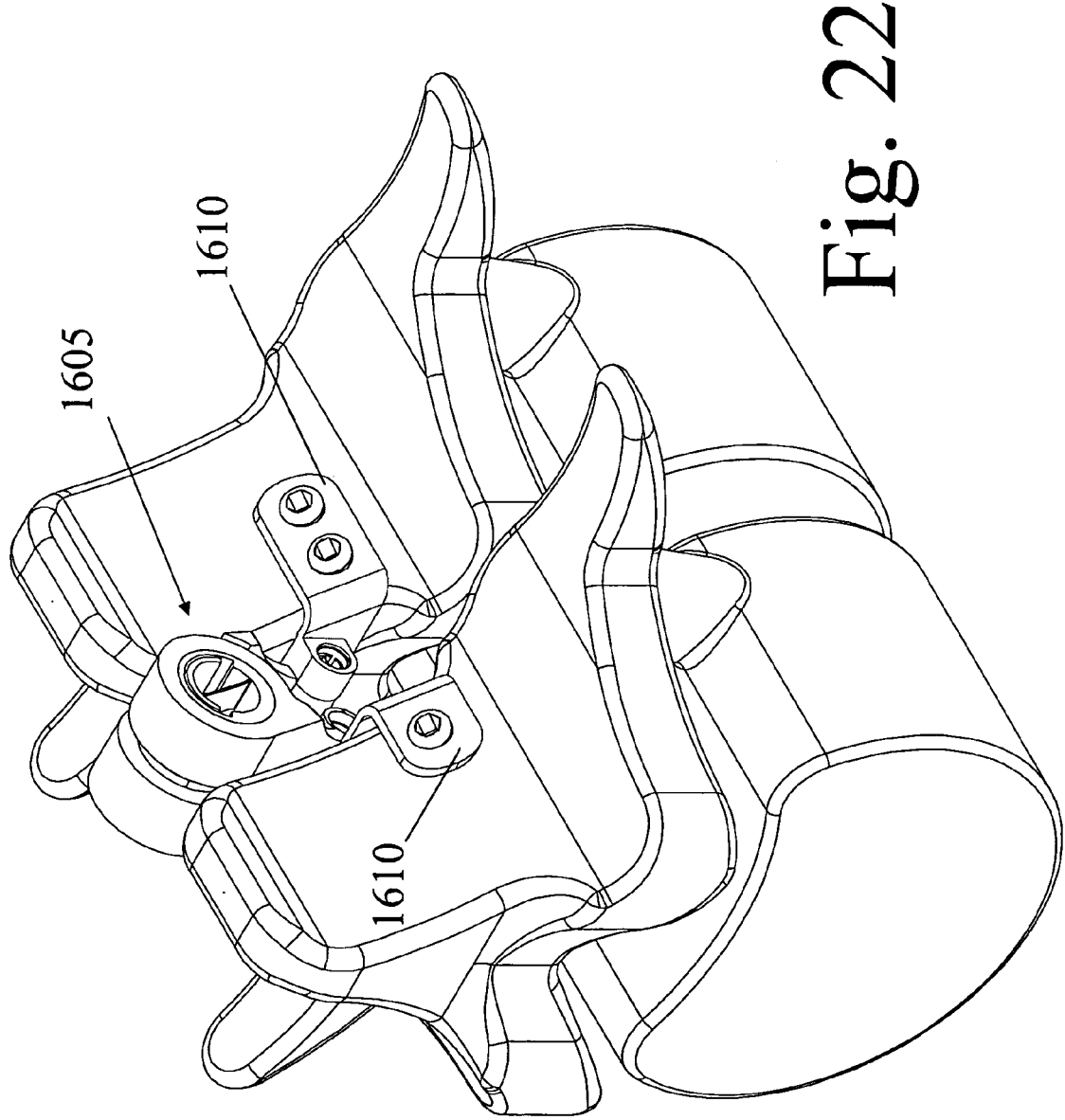
FIGS. 22-26 show another embodiment of an interspinous device.
Figure 23:
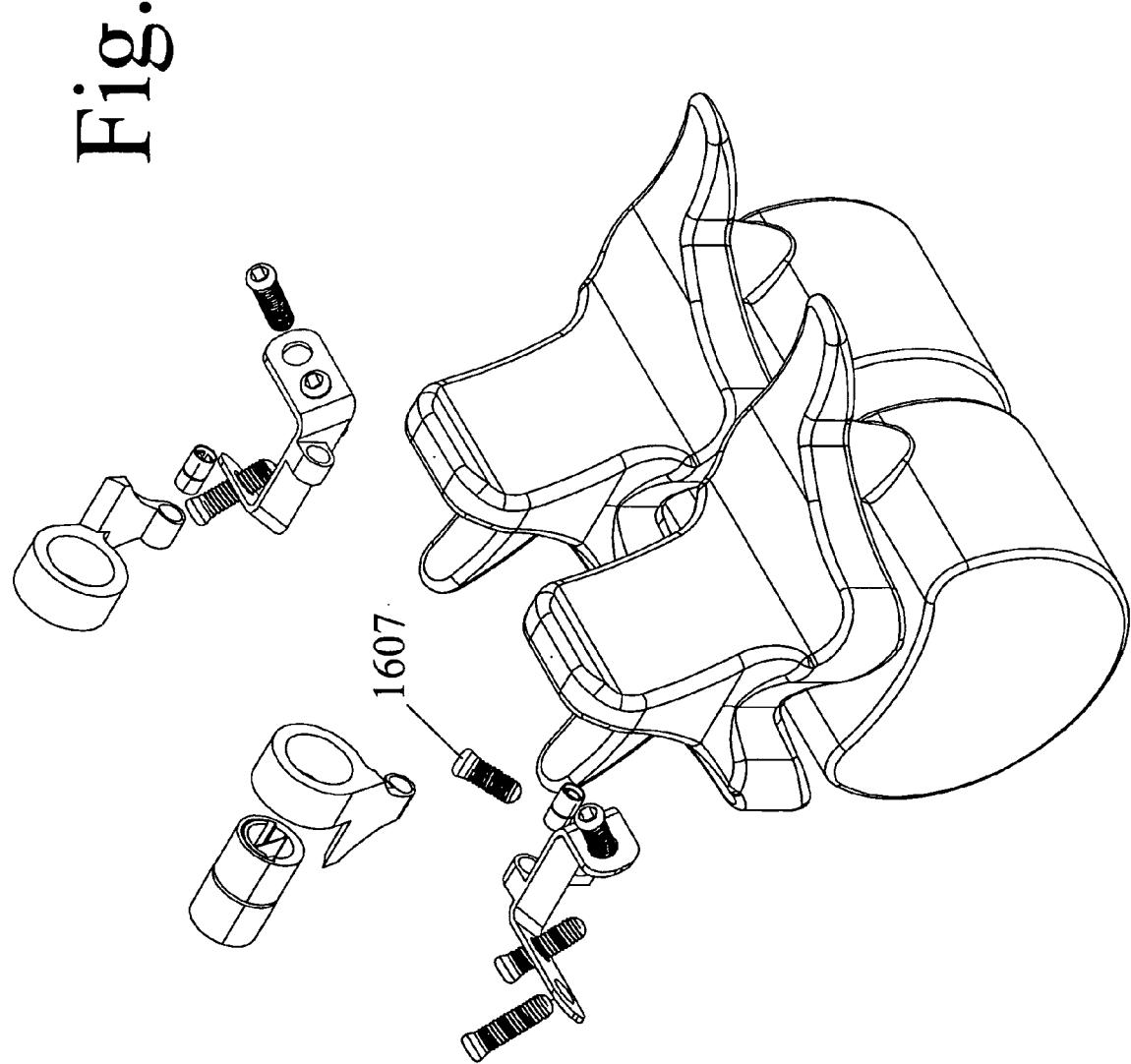
Figure 24:
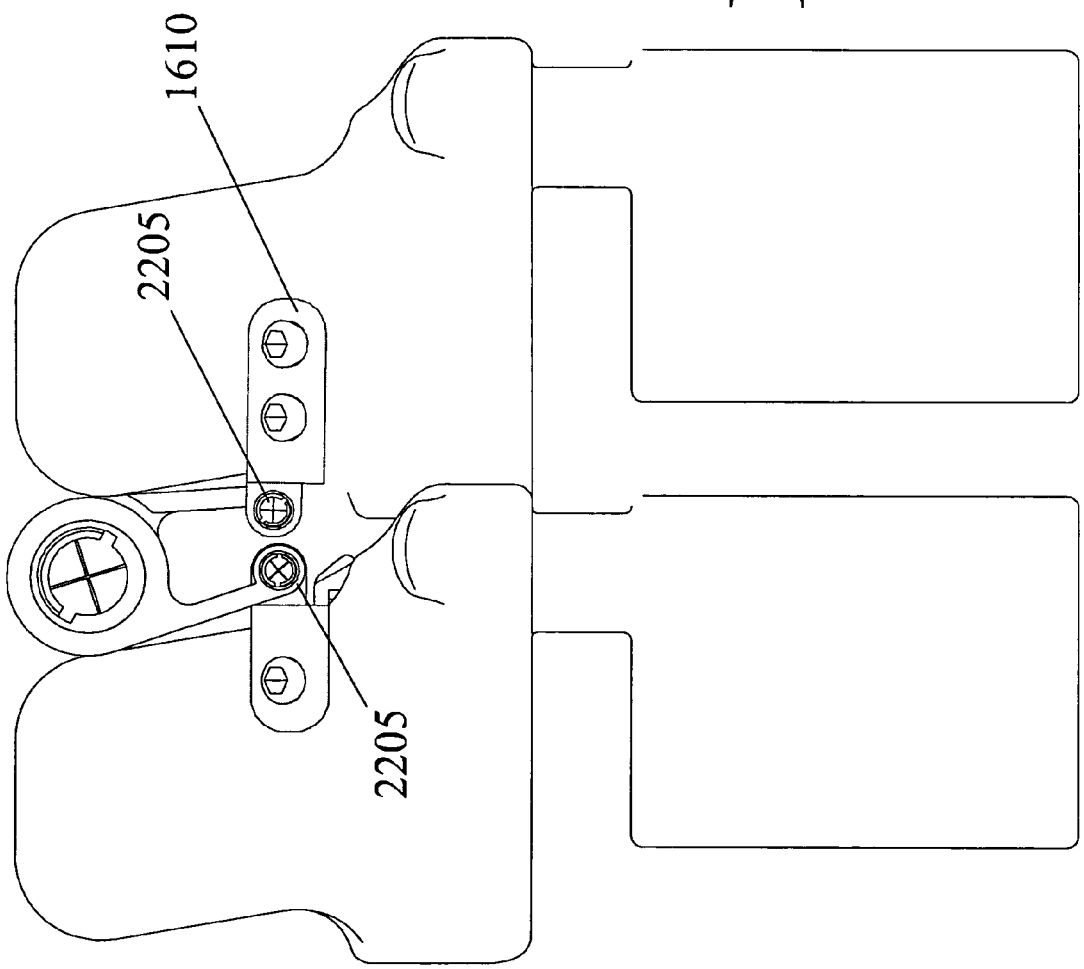
Figure 25:
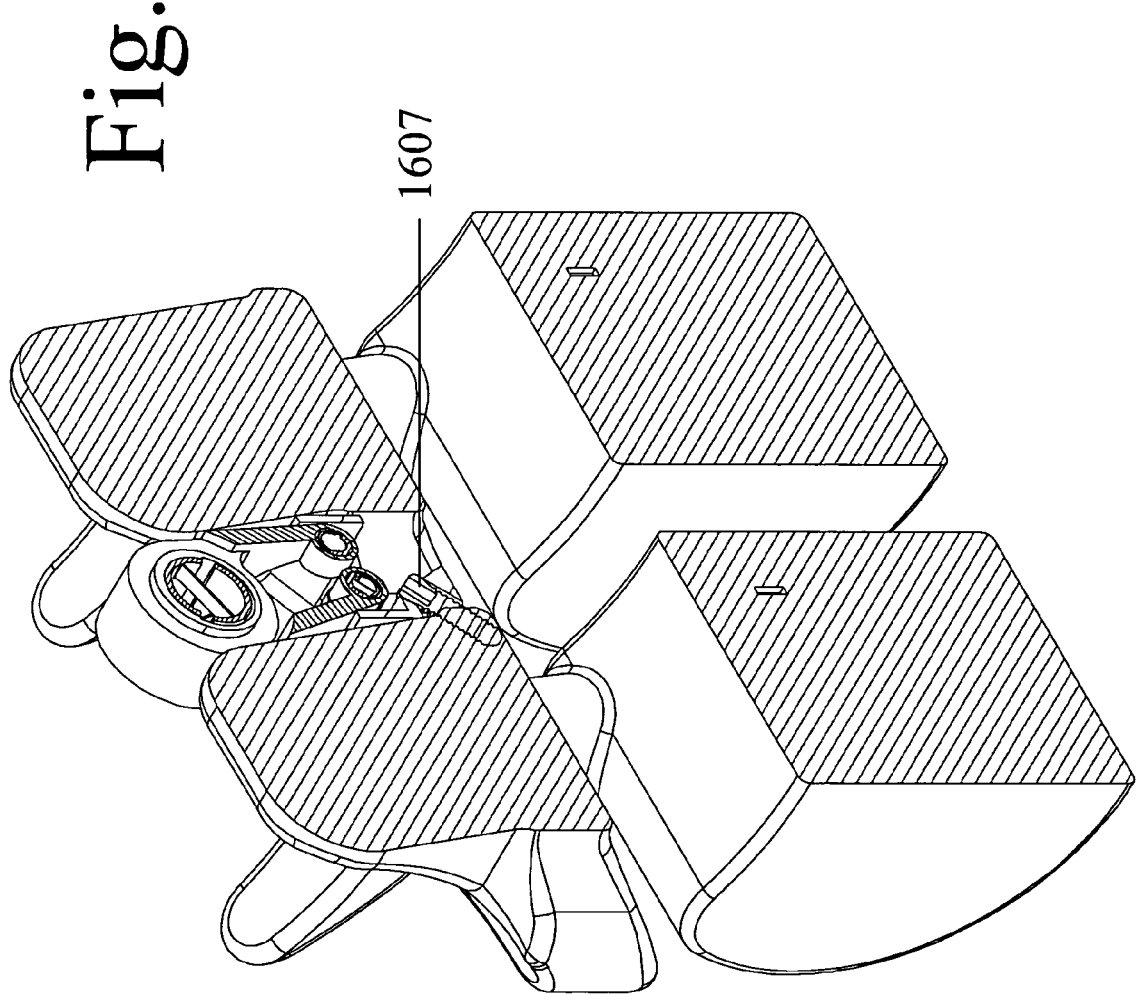

FIGS. 19-21 show another embodiment of an interspinous device that is configured for placement between the spinous processes of two adjacent vertebral bones. FIG. 19 shows a perspective view of the device mounted on vertebral bones while FIG. 20 shows a lateral view of the device mounted on vertebral bones. FIG. 21 shows cross-sectional views of the device. As in the previous embodiment, the device includes an articulating central region 1605 that is sized and shaped to fit between the spinous processes of the two adjacent vertebral bodies. The device further includes a pair of attachment regions 1610 each adapted to attach and anchor onto the spinous process of a vertebral body. In this regard, the attachment regions 1610 are sized and shaped to at least partially encircle the spinous processes in an anterior-posterior direction. The attachment regions 1610 are contoured to provide a relatively smooth fit when placed on the spinous processes.

The central region 1605 can have a variety of shapes and sizes for placement between the spinous processes. The central region 1605 includes an articulating member 1620 positioned between the spinous processes. The articulating member 1620 can have a structure as shown in FIGS. 5-6. The articulating member is configured to provide a point of articulation between the vertebral bones. It should be appreciated that additional points or locations of articulation can be provided, such as in the previously-described embodiment. The central region 1605 further includes a pair of plate members 1625 that abut the spinous processes in the implanted device.

FIGS. 22-25 show various views of another embodiment of an interspinous device that is configured for placement between the spinous processes of two adjacent vertebral bones. The device includes an articulating central region 1605 that is sized and shaped to fit between the spinous processes of the two adjacent vertebral bodies. The device further includes a pair of attachment regions 1610 each adapted to attach and anchor onto the spinous process of a vertebral body. In this regard, the attachment regions 1610 are sized and shaped to be positioned along the sides of the spinous processes. The attachment regions 1610 can have a clamp-like or "u"-shaped configuration that is positioned over the sides of the spinous processes.

Figure 26:
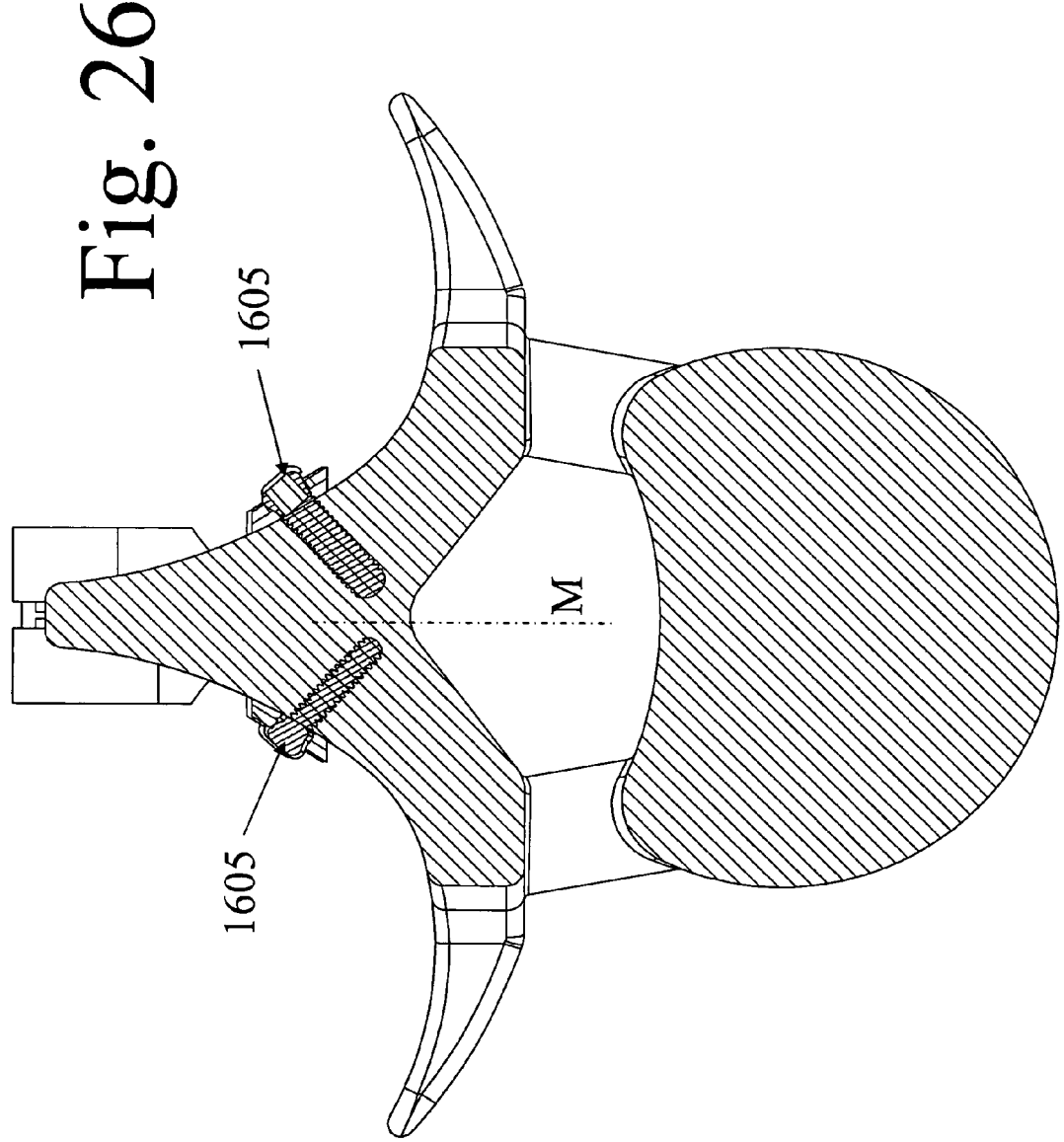

FIG. 26 is a cross-sectional view that illustrates how attachment screws attach the device to the spinous processes. A pair of bone screws 1615 extend through the attachment regions 1610 and into the spinous processes. The screws engage the interior aspect of the spinous processes at an angle to the long axis of the spinous processes. The screws follow a trajectory that preferably aims the screw tips towards the vertebral midline M. An additional screw 1607 (FIGS. 23, 25) can be inserted into the anterior-superior lip of the spinous processes.

With reference still to FIGS. 22-25, the device has at least one, and preferably three, points or locations of articulation. The articulation is provided by one or more flexible pivot members 2205 located in the central region 1605. The pivot members can have a construction as shown in FIGS. 5-6.

Figure 27:
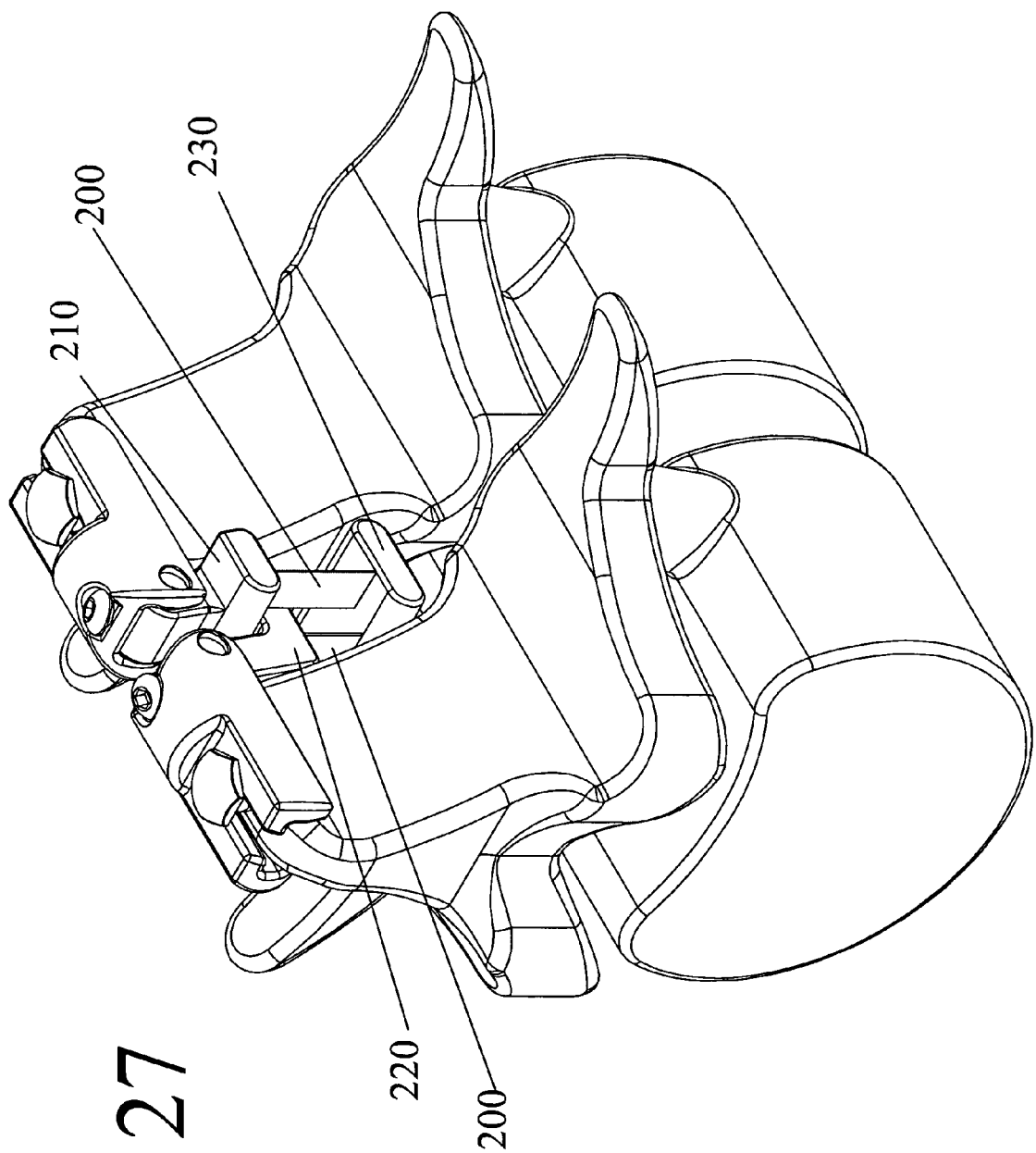
FIG. 27 shows another embodiment of a vertebral implant.
Figure 28:
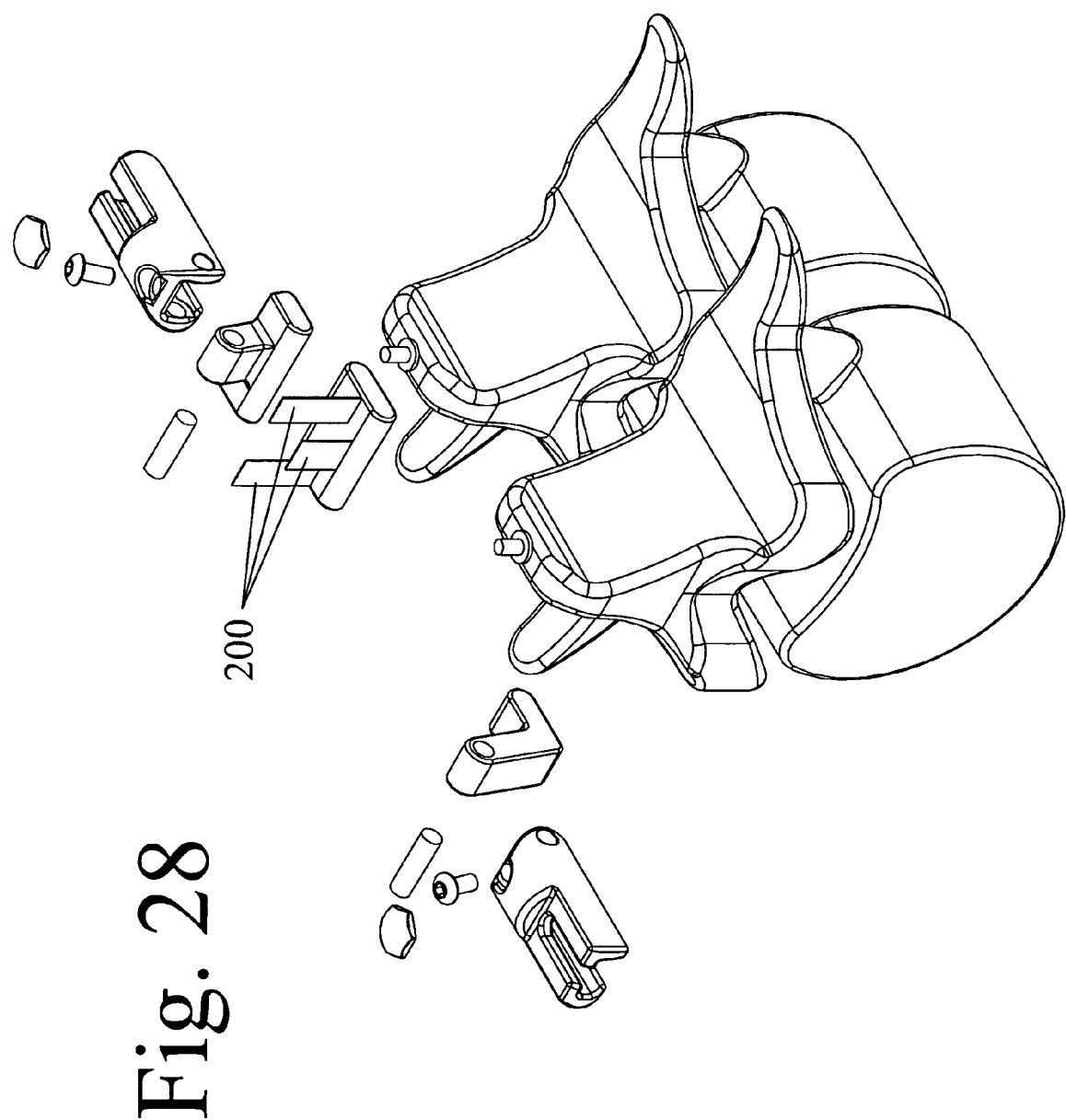
FIG. 28 shows the device of FIG. 27 in an exploded state.

There are now described and illustrated additional embodiments that use flexible plank members 200 to produce mobile devices with minimal frictional contact. FIG. 27 shows a first embodiment of such a device. As in the previous embodiments, the device includes an articulating central region that is sized and shaped to fit between the spinous processes of the two adjacent vertebral bodies. The device further includes a pair of attachment regions each adapted to attach and anchor onto the spinous process of a vertebral body. The central region uses flexible plank members comprised of elongate, planar elements that can flex. The device has a cross member that attaches at opposite end to bone screw assemblies. The device can attach to the spinous processes using screws. While illustrated as attaching onto the spinous process using screws positioned along the long axis of the spinous process, the device may be alternatively attached to the bone using any of the previously illustrated fixation methods or any other applicable method that is known in the art. FIG. 28 shows the device of FIG. 27 in an exploded state. FIGS. 29A and 29B show the device in cross-section.

The device includes attachment members 210, 220, and 230 that fit between the spinous processes. The attachment members are inter-connected by the flexible plank members 200. A first member 210 is affixed onto one vertebra while a second member 220 is attached onto a second vertebra. A member 230 is placed within the space between the spinous processes at a distance from each of members 210 and 220 and attached to the former by two side flexible plank members 200 and to the latter by a central flexible plank member 200. The configuration of flexible plank members and attachment members permit particular movements and limit other types of movement. It should be appreciated that the quantity and shape of the flexible plank members can vary.

Figure 30A:
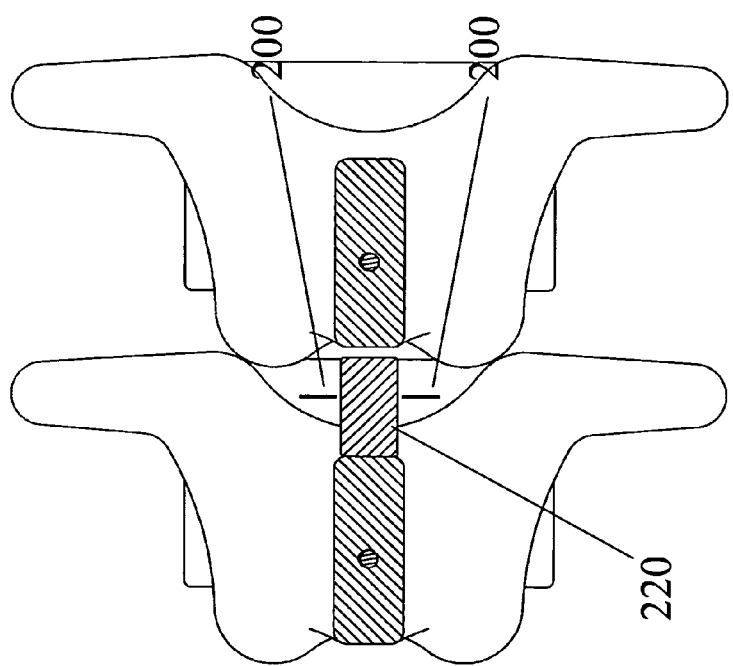
FIG. 30A shows the vertebral bodies in partial flexion.
Figure 30B:
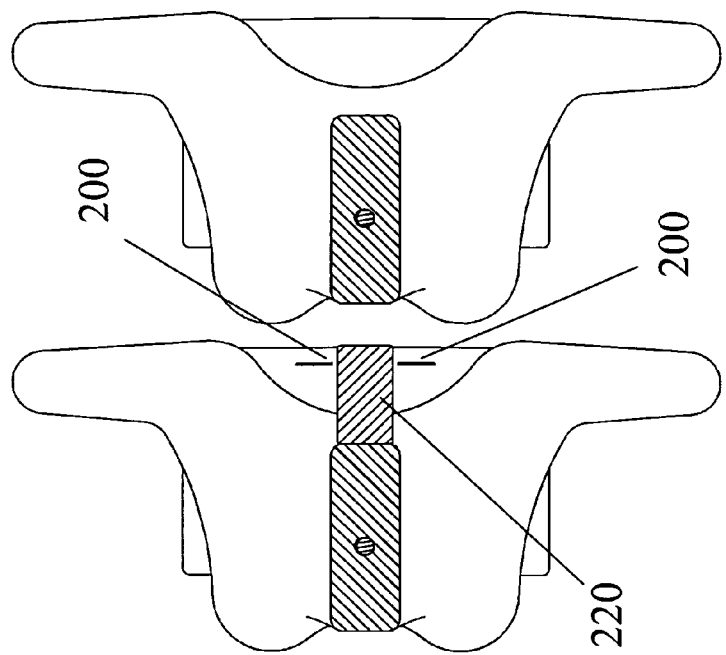
FIG. 30B shows the vertebral bodies in full flexion.

In specific, significant movement of the vertebra towards each other is prevented by the interaction of members 210 and 220. That is, vertebral extension is limited by the collision of member 210 and 220 with one another. Alternatively, member 230 may be enlarged and sized to limit vertebral extension by directly maintaining the distance between the spinous processes of the two vertebras. The members are sized and shaped to provide a level of movement therebetween. The movement of the vertebra away from one another is permitted but reversibly opposed by the action of flexible members 200. The anterior translation of upper vertebra relative to the lower vertebra is prevented by the interaction of member 210 and 220. Lateral flexion of the vertebral bodies is permitted to a limited degree. Vertebral rotation is limited by the shape of the flexible members 200 since rotation requires flexure of members 200 towards one of the long sides of each plank member. Rotation is also opposed by the collision of the medial surface of each of the laterally-placed members 200 and the lateral surfaces of medially-placed member 220. The foregoing is illustrated in cross-section in FIG. 30A where the vertebral bodies are in partial flexion and in FIG. 30B where the vertebral bodies are in full flexion. Note that the amount of rotation does not vary with the extent of flexion.

Figure 32A:
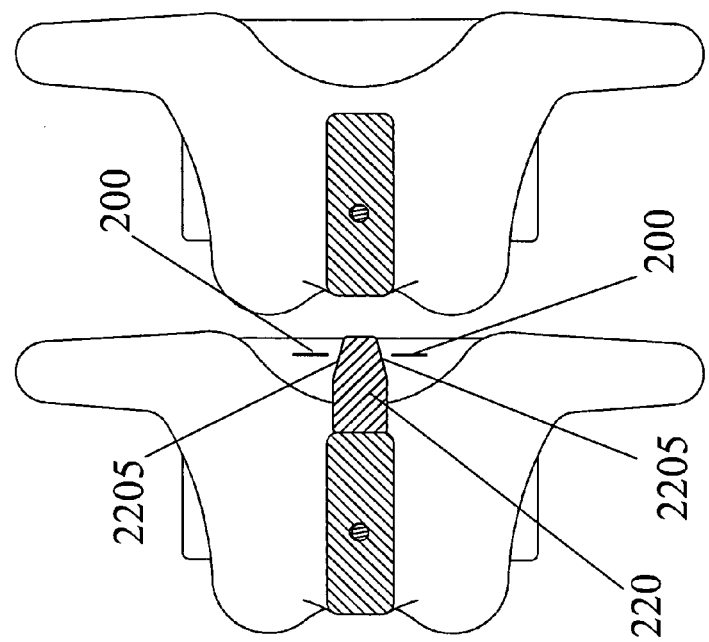
FIG. 32A shows the vertebral bodies in partial flexion.
Figure 32B:
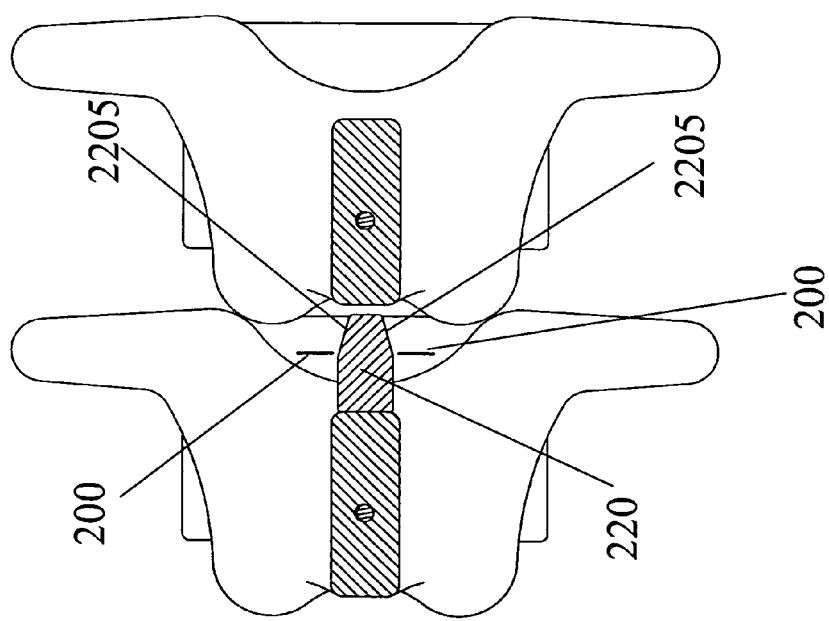
FIG. 32B shows the vertebral bodies in full flexion.

FIG. 31 shows another embodiment of the flex member 220. This embodiment has a "V"-shaped configuration with a thickness defined by side walls 2205. Along at least a portion of the member 220, the side walls 2205 are non-parallel. For example, this embodiment has side walls 2205 that converge towards one another while the side walls 2205 of member 220 of the previous embodiment are parallel and non-convergent. With this modification, the present embodiment recreates physiologic spinal motion by allowing the extent of vertebral rotation to increase with progressive vertebral flexion. This is illustrated in cross-section in FIG. 32A where the vertebral bodies are in partial flexion and in FIG. 32B where the vertebral bodies are in full flexion. Note that the distances between the medial edge of each of members 200 and lateral side walls 2205 of member 220 increase with flexion and permit a greater range of vertebral rotation.

Figure 33:
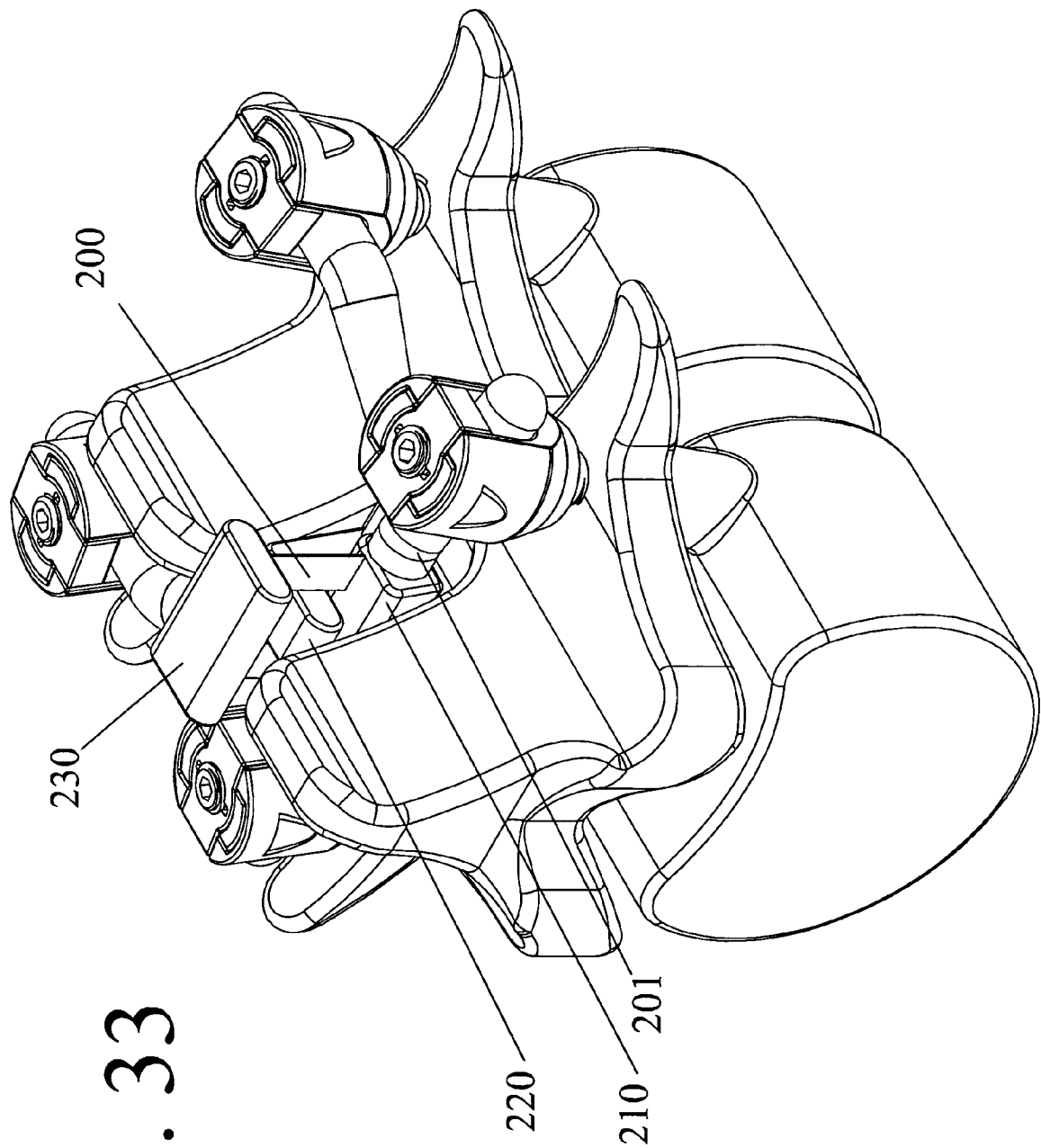

FIGS. 33 and 34 illustrate perspective and cross-sectional views of another embodiment of an interspinous device. Like the prior two embodiments, attachment members 210, 220, and 230 are inter-connected by flexible plank members 200 that extend between the attachment members. A member 210 is affixed onto one vertebra while member 220 is attached onto a second vertebra. Unlike the prior embodiments, the device is attached to the vertebral bone using bone screws or similar fasteners that attach onto the pedicle portion of the vertebrae. A bone screw also attaches to the spinal process. The member 230 is placed at a distance from each of members 210 and 220 and attached to the former by two side flexible plank members 200 and to the latter by a central flexible plank member 200. The device is functionally similar to the prior two embodiments.

There are now described multiple embodiments of mobile devices that are placed within the disc space between two vertebral bodies and used to at least partially replace and/or augment the function of the native disc. Each of these embodiments uses one or more of the flexible pivot members (articulation members) such as the type shown in FIGS. 5 and 6. FIG. 35 illustrates a coronal section through embodiment of such a mobile device. The device contains a top surface 440, a bottom surface 442, cylindrical members 444 and 446, link members 448 and 450 as well as multiple flexible pivot members of the type shown in FIGS. 5 and 6. The cylindrical members 444 and 446 slidably reside within cylindrical channels in the upper surface of member 442. The articulations between the cylindrical members and cylindrical channels permit extension and anterior flexion of the implanted device and the attached vertebral bodies. In addition, the actions of the flexible pivot members 110 permit relative vertical movement of surfaces 440 and 442 and impart a shock-absorbing quality to the device. Finally, movement in the coronal plane recreates the lateral flexion movement of the natural disc but rotation is effectively prevented.

Figure 36A:
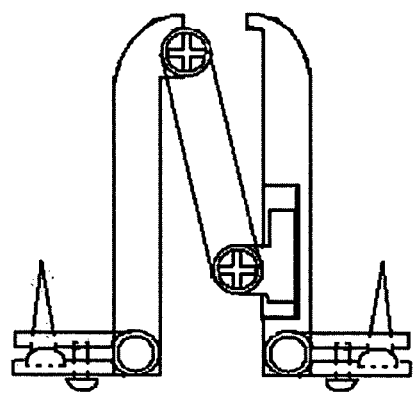
FIGS. 36A-36C show another embodiment of an implant device.
Figure 36C:
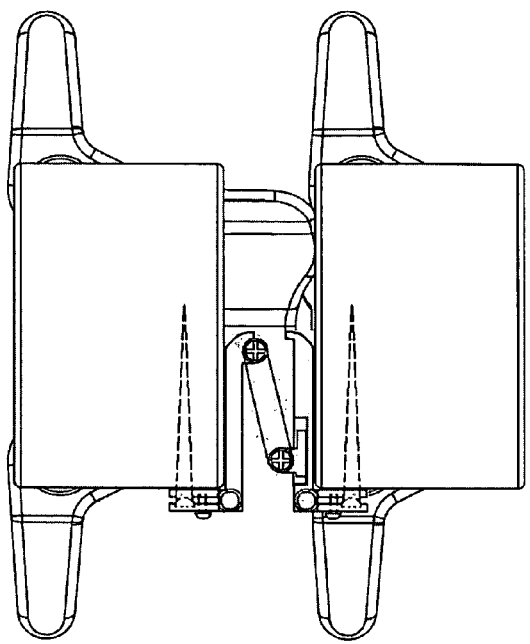
Figure 36B:
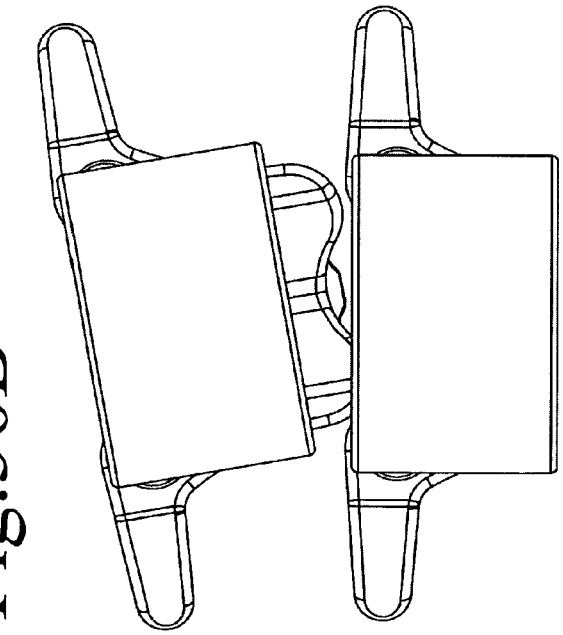

FIG. 36A is another embodiment that is similar to the previous embodiment. This embodiment is structured such that it is effectively one half of the previous embodiment. The device is particularly useful in the correction of vertebral coronal plane mal-alignment (i.e., scoliosis). FIG. 36B shows a mal-aligned vertebral segment and FIG. 36C shows the segment with the device of 36A implanted. The device is adapted to re-align the mal-aligned vertebral segment when positioned between the vertebral bodies. As in the previous embodiments, the top and bottom surfaces can move relative to one another in response to loads. Further, device attachments onto the sides of the vertebral bones provide additional points of fixation.

Figure 37:
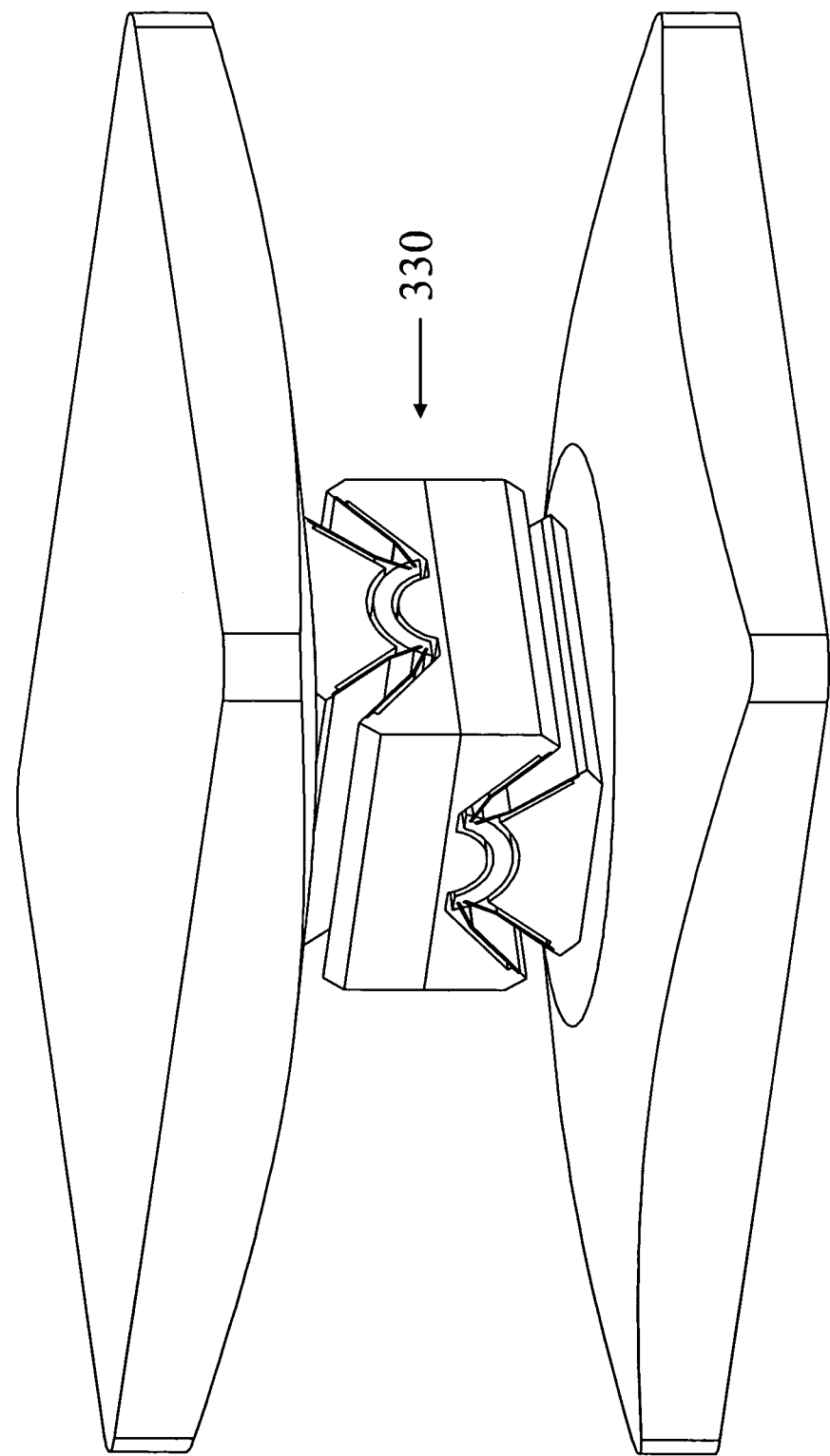
Figure 40A:
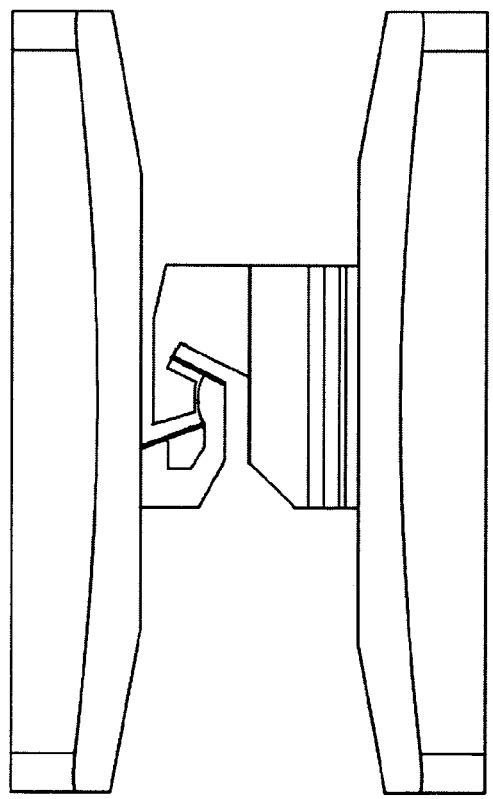
Figure 40B:
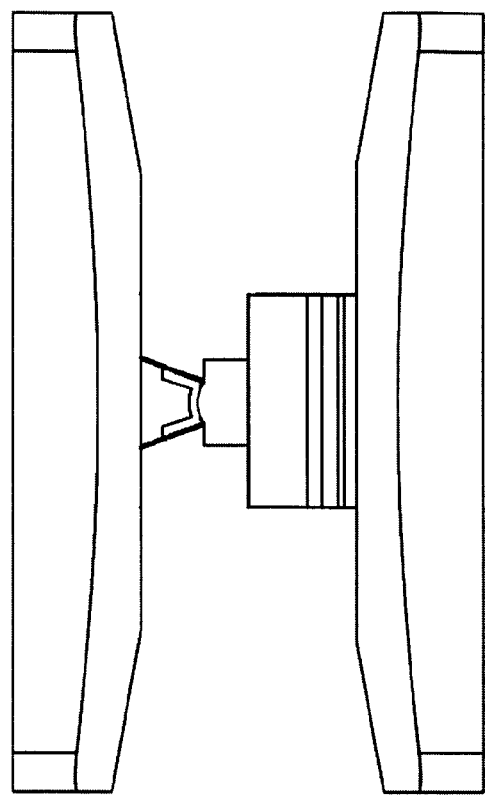

FIGS. 37-40 illustrate multiple embodiments of mobile devices that are placed within the disc space between two vertebral bodies and used to at least partially replace and/or augment the function of the native disc. Each device embodiment uses one or more flexible plank members with a central mobile surface assembly 330 positioned therebetween. The assembly 330 is adapted to articulate in response to loads to provide relative movement between the flexible plank members. FIG. 37 shows a perspective view of one embodiment while FIG. 38 illustrates additional views of the embodiment. FIG. 39 shows an exploded view of the central mobile surface assembly 330. An upper segment 310, middle segment 320 and lower segment 325 are interconnected by flexible plank members 315 as shown and collectively make up the upper one-half of assembly 330. The flexible plank members 315 are spaced from one another to provide space for relative movement and articulation of the plank members 315. The lower one-half of the assembly is similarly configured but the moving members are situated perpendicular to the upper one-half of the assembly. FIGS. 40A and 40B show alternative mobile assembly embodiments.

Figure 41:
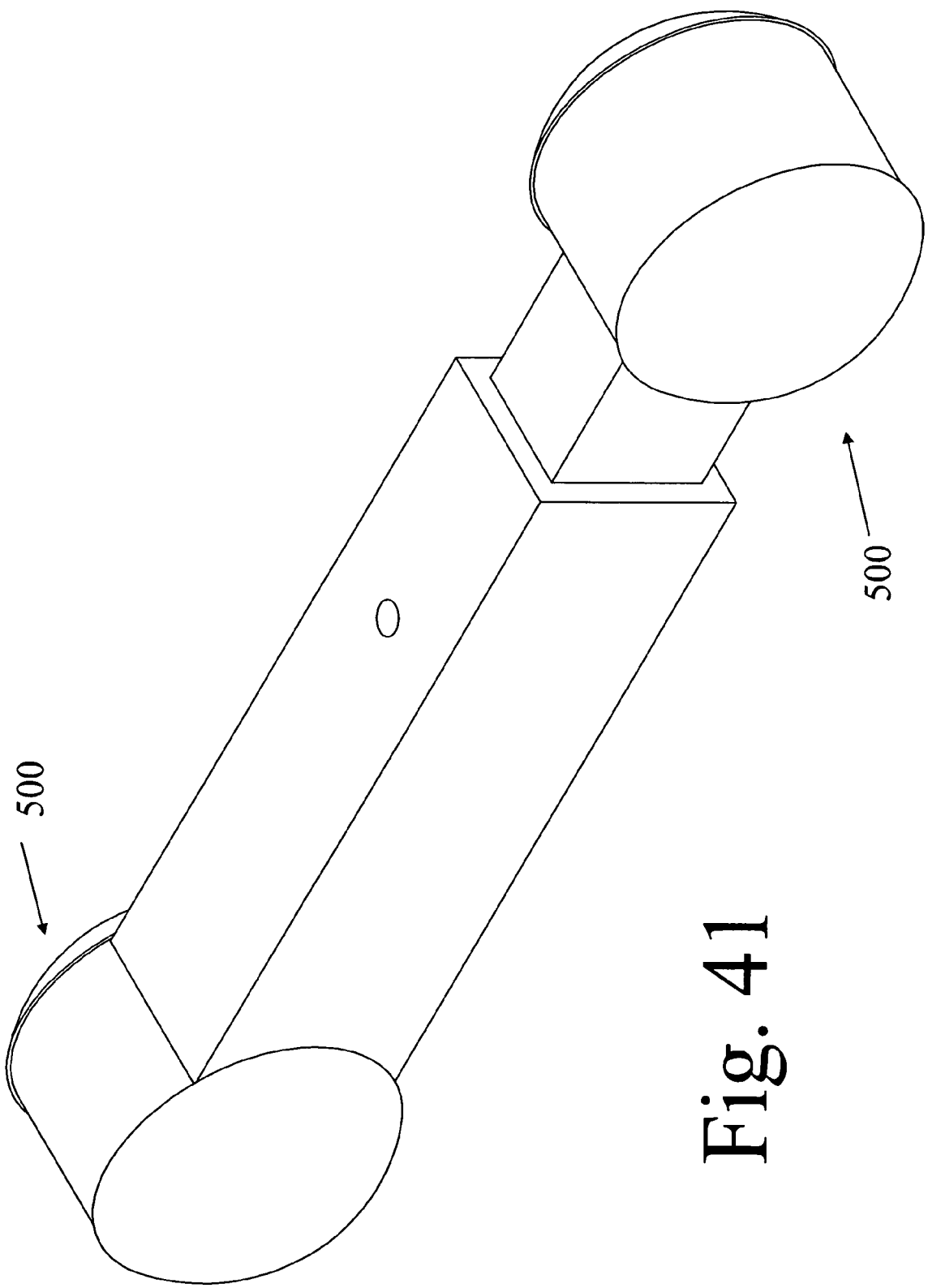
FIG. 41 illustrates a perspective view of the a dynamic rod.
Figure 42:
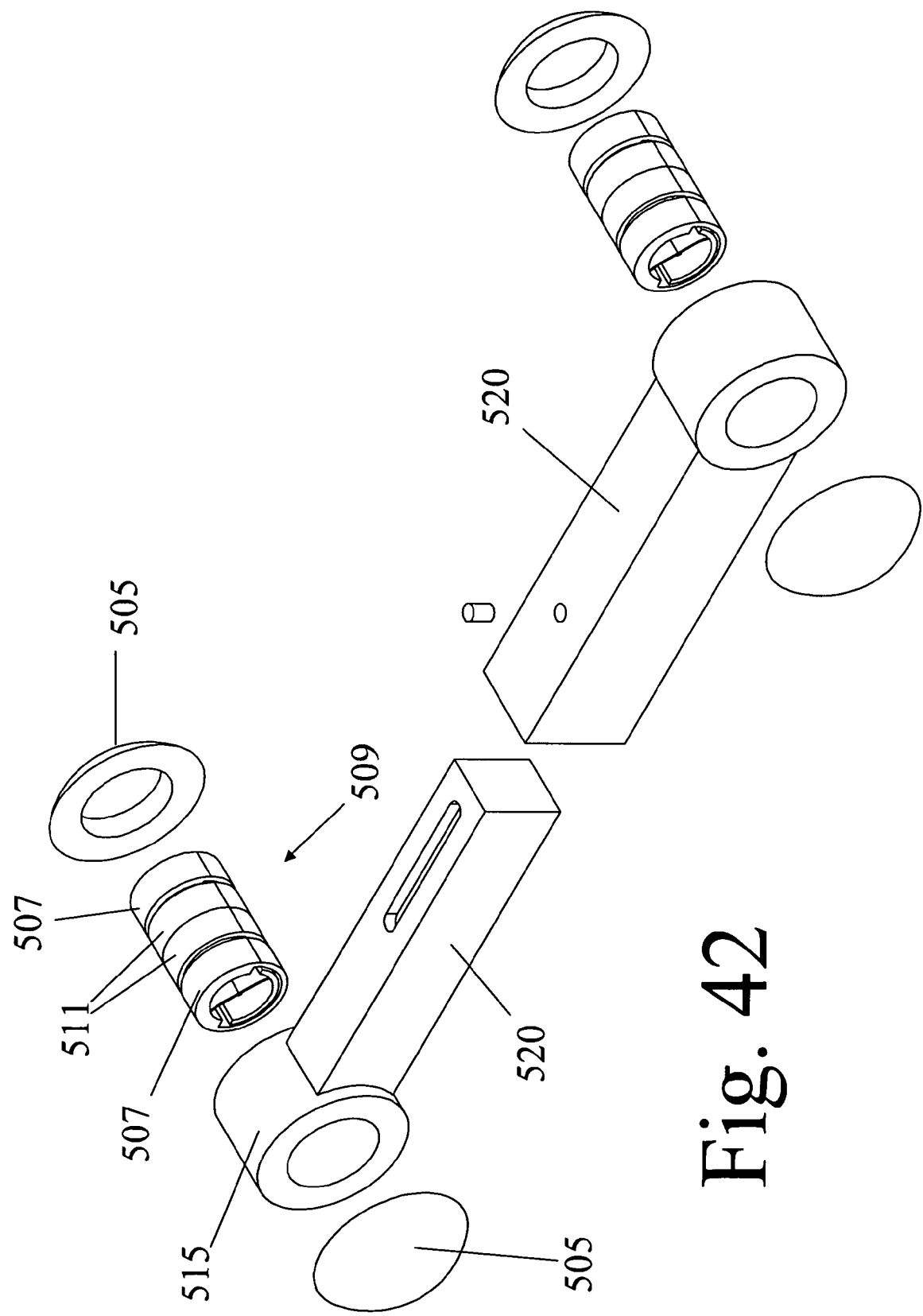
FIG. 42 shows the dynamic rod in an exploded state.

FIGS. 41 to 55 show a dynamic rod. The rod is adapted to be linked at opposite ends to bone screw assemblies which attach to vertebral bones. The rod is dynamic in that it can change shape in response to loads. The device is preferably attached to bone using a screw assembly such as shown in the example of FIG. 43. FIG. 41 illustrates a perspective view of the device while FIG. 42 shows the device in an exploded state. The opposed ends of the device each have a head that couples to the bone screw assembly.

Figure 44:
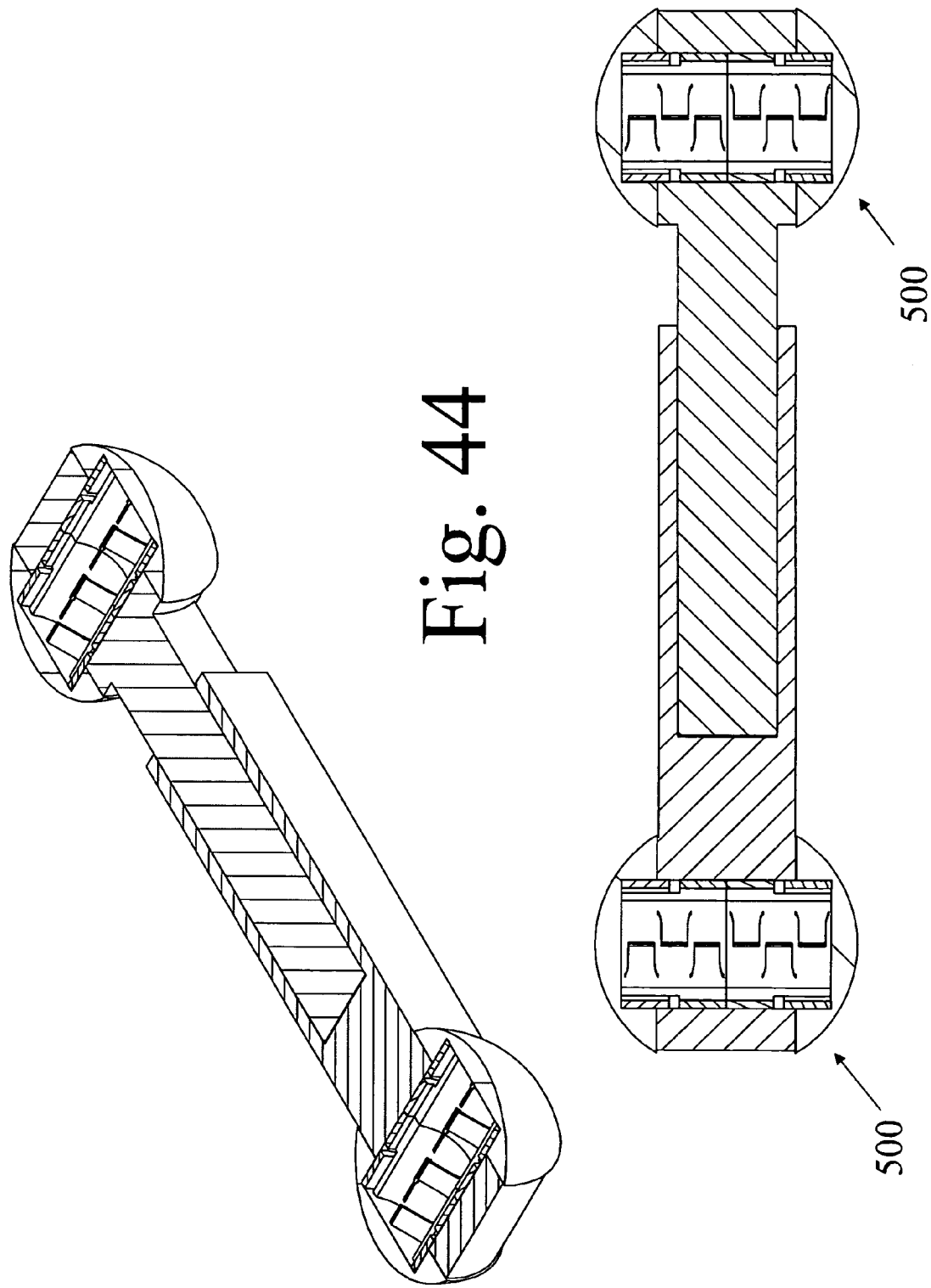
FIG. 44 shows cross-sectional views of the dynamic rod.
Figure 45:
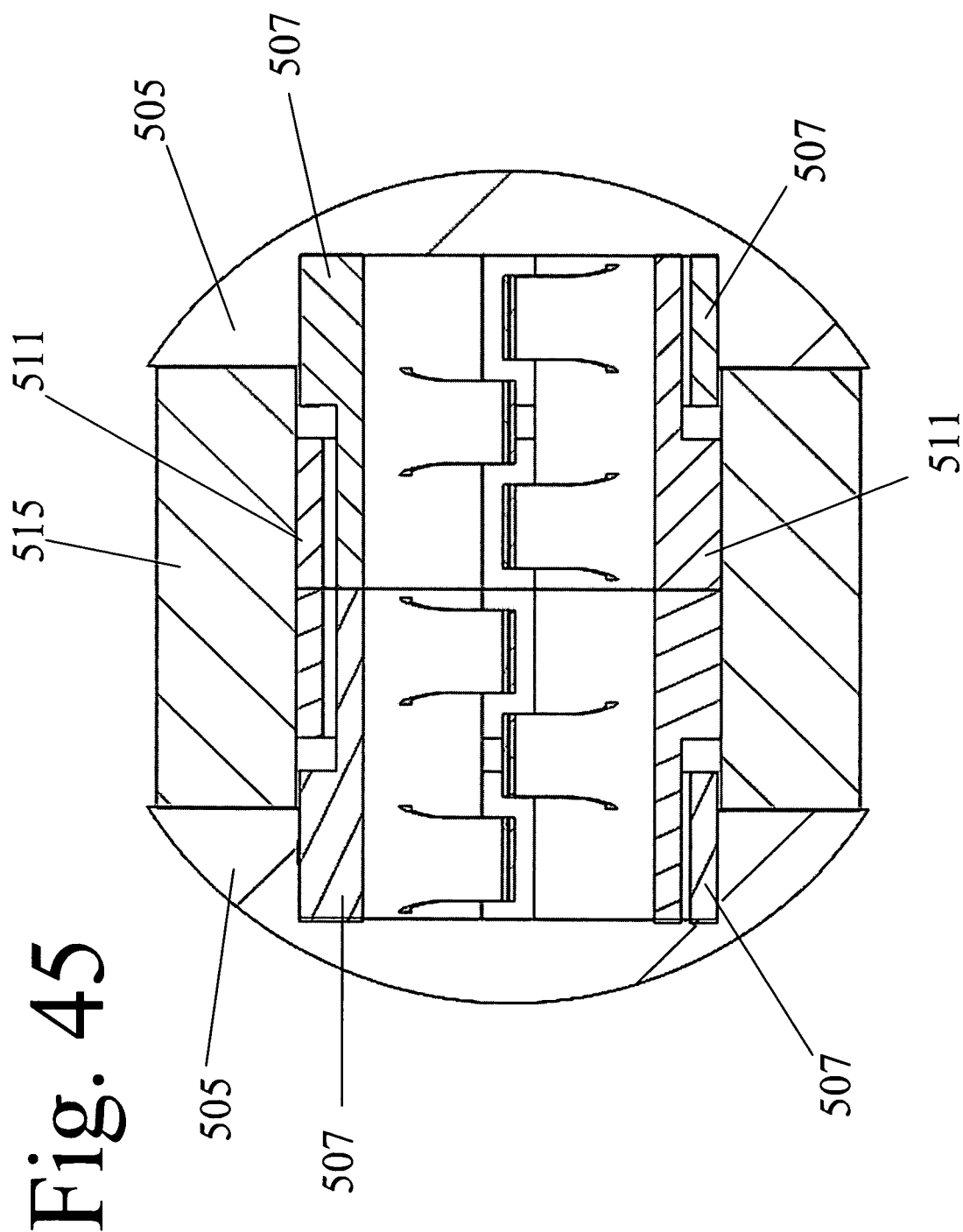
FIG. 45 shows a flexible pivot of the dynamic rod.
Figure 46:
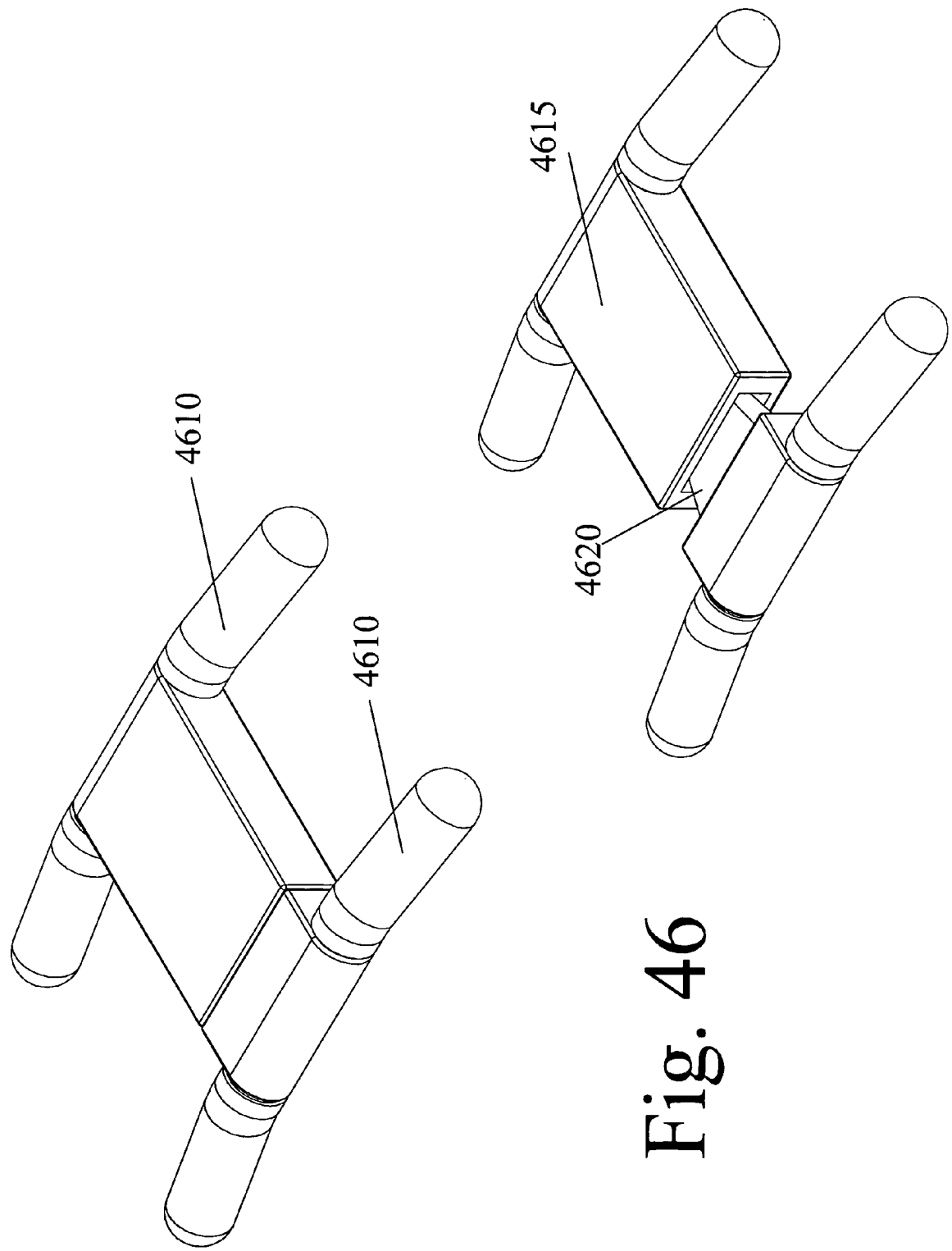

FIG. 44 shows cross-sectional views of the device. In use, each end 500 is paced within a receiving porting of a bone screw assembly (such as shown in FIG. 43). After the devices are placed into the desired position, the locking screw of the screw assembly is tightened thereby locking both spherical segments 505 of ends 500 relative to the remainder of the screw assembly. Each end segment 505 is rigidly affixed to the end segments 507 of flexible pivot 509 (FIG. 45). The middle segment 511 of pivot member 509 is rigidly affixed to the middle segment 515 (FIG. 45). The configuration allows the movement of middle segment 515 relative to immobilized end segments 505 based on the action of flexible pivot 509. Each of rectangular rod 520 can move relative to one another in the direction of the long axis of the rods.

Figure 47:
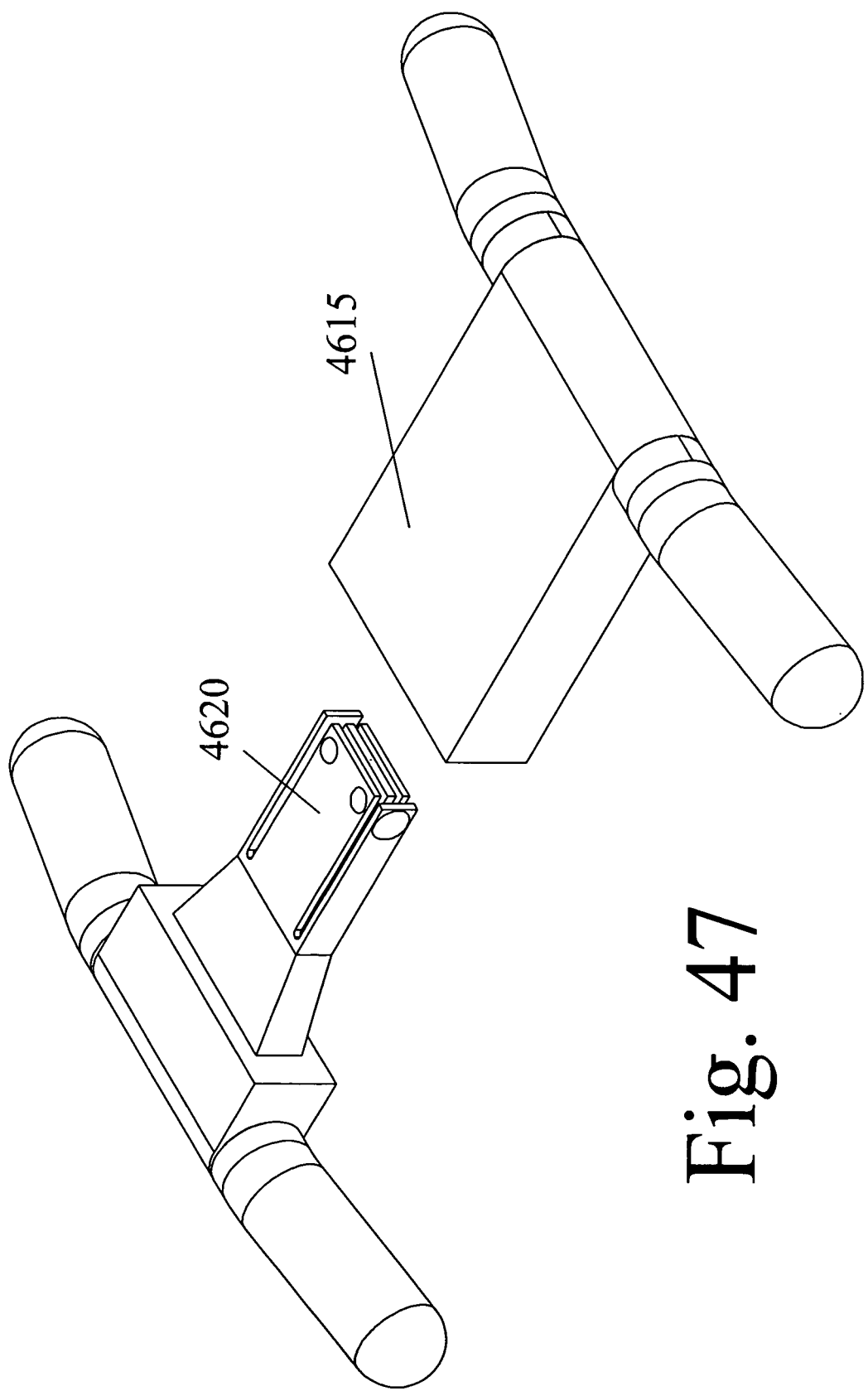

In another embodiment, FIGS. 46-49 show a dynamic rod assembly that includes two rod members 4610 that are movably attached to one another via a dynamic pyramidal connector. The connector is formed of two pieces 4615 and 4620 that can slidably move relative to one another in a male-female relationship. FIG. 47 shows the device with the pieces 4615 and 4620 separated from one another. The piece 4620 is formed of a plurality of interconnected plank members that can flex relative to one another so as to change the shape of the piece 4620. The piece 4620 fits into a cavity within the piece 4615, as shown in the cross-sectional views of FIGS. 48 and 49. When positioned in the cavity, the planks of piece 4620 expand outward such that the piece 4620 is retained within the cavity. Movement of the male member relative to the female member is at lease partially resisted by the action of the plank members.

The disclosed devices or any of their components can be made of any biologically adaptable or compatible materials. Materials considered acceptable for biological implantation are well known and include, but are not limited to, stainless steel, titanium, tantalum, shape memory alloys, combination metallic alloys, various plastics, resins, ceramics, biologically absorbable materials and the like. Any components may be also coated/made with osteo-conductive (such as demineralized bone matrix, hydroxyapatite, and the like) and/or osteoinductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. An implant adapted to dynamically stabilize two or more vertebral bones, comprising:
    a first attachment member configured to attach onto a first vertebral bone;
    a second attachment member configured to attach onto a second vertebral bone; and
    a pivot member configured to permit movement between the first and second attachment members, comprising:
        a first cylindrical member that extends from a first end to a second end along a first central axis and comprising an outer wall and an internal cavity; and
        a second cylindrical member that extends from a first end to a second end along a first central axis and comprising an outer wall and an internal cavity;
    wherein a monolithic extension of one of the ends of the first cylindrical member is positioned within the internal cavity of the second cylindrical member, but separated from direct abutment therewith;
    wherein at least one malleable member extends from a surface of the monolithic extension to an internal surface of the second cylindrical member; and
    wherein the outer wall of the second hollow cylindrical member is configured to rotate relative to the monolithic extension.

2. The implant of claim 1, further comprising a hinge member configured to be positioned between one of the first and second attachment members and the pivot member, the at least one malleable member configured to reversibly return the hinge member to a neutral position after dissipation of a force acting upon it.

3. The implant of claim 1, wherein the at least one malleable member is configured to dampen movement between the first and the second vertebral bones.

4. The implant of claim 1, wherein the first cylindrical member has a range of rotation relative to the second cylindrical member between −30 and +30 degrees.

5. The implant of claim 1, wherein the pivot member is configured to prevent anterior displacement of the first vertebral bone relative to the second vertebral bone.

6. The implant of claim 1, wherein the pivot member is configured to limit extension between the first and the second vertebral bones.

7. The implant of claim 1, wherein the first attachment member configured to rigidly affix onto a spinous process of the first vertebral bone.

8. The implant of claim 7, wherein at least one rigid bone fixation member is configured to extend from the first attachment member and penetrate a surface of a spinous process of the first vertebral bone.

9. An implant adapted to dynamically stabilize two or more vertebral bones, comprising:
    a first attachment member adapted to attach onto a first vertebral bone;
    at least one second attachment member adapted to attach onto at least one additional vertebral bone; and
    at least one pivot member configured to connect the first and second attachment members, comprising:
        a first member comprising an outer surface, an internal cylindrical surface and a first central longitudinal axis;
        a second member comprising an outer surface, an internal cylindrical surface and a second central longitudinal axis, the first and second axes configured to coaxially align and form a common axis of rotation between the first and second members; and
        at least one malleable member configured to extend from the internal cylindrical surface of the first member to the internal cylindrical surface of the second member, the malleable member configured to resist rotational movement between the first and second members about the common axis;
    wherein at least one of the attachment of the first attachment member to the first vertebral bone and the attachment of the second attachment member to the at least one additional vertebral bone comprises attachment via one or more bone screws and at least one of the first and second attachment members further comprises at least one aperture for receiving the one or more bone screws therein.

10. The implant of claim 9, wherein at least one of the first and second attachment members is configured to connect to the pivot member via a coupling.

11. The implant of claim 10, wherein one or more substantially cylindrical articulation locations are positioned in corresponding openings of the pivot member.

12. The implant of claim 9, wherein the pivot member is sized and shaped to fit at least partly between a spinous processes of the first and second vertebral bones.

13. The implant of claim 9, wherein the pivot member is further configured to limit an amount of vertebral extension.

14. The implant of claim 9, wherein the pivot member is further configured to resist at least one of anterior or posterior displacement of the first and second vertebral bones.

15. The implant of claim 9, further comprising one or more hinge members configured to be positioned between one of the first and second attachment members and the pivot member.

16. The implant of claim 9, wherein the pivot member is further configured to dampen movement between the first and second vertebral bones.

17. The implant of claim 9, wherein the malleable member is configured to reversibly return the pivot member to a neutral position after dissipation of a force acting upon it.

18. The implant of claim 9, wherein the first and second members are separated from direct abutment with one another.

19. The implant of claim 9, wherein the pivot member provides frictionless rotation between the first and second members.

20. An implant adapted to stabilize two or more vertebral bones, comprising:
    a first attachment member adapted to attach onto a first vertebral bone;

at least one second attachment member adapted to attach onto at least one additional vertebral bone; and at least one member configured to connect the first and second attachment members and dampen motion therebetween, comprising:

a first member that extends from a first end to a second end along a first central axis and comprising an outer surface and an internal cavity;

a second member that is separated from direct abutment with the first member and comprising an outer surface, an internal cavity, and a second longitudinal axis, the first and second longitudinal axes configured to coaxially align and form a common axis of rotation between the first member relative to the second member, and the first member further comprising a monolithic extension of one of the ends thereof that is configured to be positioned within the internal cavity of the second member; and at least one malleable member configured to extend from an internal surface of the extension to a surface of the internal cavity of the second member, the malleable member configured to bias the rotation of the first member towards a neutral position relative to the second member.

21. The implant of claim 20, wherein the malleable member resists rotational movement between the first and second members about the common axis.

22. The implant of claim 20, wherein the outer surface of the second member is configured to concentrically rotate relative to the extension.

* * * * *